US009320636B2

(12) United States Patent
Shirogauchi et al.

(10) Patent No.: US 9,320,636 B2
(45) Date of Patent: Apr. 26, 2016

(54) SUPPORT DEVICE, OPERATION SUPPORT DEVICE, AND MUSCLE STRENGTH TRAINING SUPPORT DEVICE

(71) Applicant: Panasonic Corporation, Osaka (JP)

(72) Inventors: Go Shirogauchi, Kyoto (JP); Hiromichi Fujimoto, Nara (JP); Yoshiaki Ueda, Osaka (JP); Makoto Konishi, Osaka (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 14/412,806

(22) PCT Filed: Jun. 25, 2013

(86) PCT No.: PCT/JP2013/003973
§ 371 (c)(1),
(2) Date: Jan. 5, 2015

(87) PCT Pub. No.: WO2014/006848
PCT Pub. Date: Jan. 9, 2014

(65) Prior Publication Data
US 2015/0190261 A1   Jul. 9, 2015

(30) Foreign Application Priority Data

Jul. 5, 2012   (JP) ................... 2012-151033

(51) Int. Cl.
*A63B 21/00*   (2006.01)
*A63B 21/005*   (2006.01)
(Continued)

(52) U.S. Cl.
CPC ............... *A61F 5/0102* (2013.01); *A61B 5/224* (2013.01); *A61H 1/02* (2013.01); *A63B 21/0058* (2013.01);
(Continued)

(58) Field of Classification Search
CPC ................... A63B 21/00076; A63B 21/00181; A63B 21/0058; A63B 21/0059; A63B 21/153; A63B 21/4005; A63B 21/4035; A63B 21/4043; A63B 23/12; A63B 23/1209; A63B 23/1245; A63B 23/1281; A63B 24/0062; A63B 24/0089; A63B 2024/0093; A63B 2220/51; A63B 2230/605; A61H 1/0274; A61H 1/0285; A61H 2201/1635; A61H 2201/1638; A61H 2201/165; A61H 2201/1652; A61H 2201/5061
See application file for complete search history.

(56) References Cited

U.S. PATENT DOCUMENTS

2005/0061072 A1   3/2005   Ambrosone
2006/0079817 A1   4/2006   Dewald et al.
(Continued)

FOREIGN PATENT DOCUMENTS

CN   102410901   4/2012
DE   10 2007 038 755   6/2008
(Continued)

OTHER PUBLICATIONS

International Search Report issued Aug. 13, 2013 in International (PCT) Application No. PCT/JP2013/003973.
(Continued)

*Primary Examiner* — Oren Ginsberg
(74) *Attorney, Agent, or Firm* — Wenderoth, Lind & Ponack, L.L.P.

(57) ABSTRACT

A support device includes: a force measurement sensor structure which includes a shaft having first and second end sections, an intermediate element movably provided between the first and second end sections, first and second elastic members respectively provided between the first end section and the intermediate element and between the second end section and the intermediate element, a linear potentiometer detecting the one dimensional direction position of the intermediate element, and a gripping unit transmitting a force to the intermediate element in an interlocking manner with movement of upper or lower limb; a drive unit changing a load applied to the intermediate element; a control unit controlling the drive unit; and a wearable unit including a front frame provided on a front side of a user, a rear frame connected to the front frame, provided on a rear side of the user, and supporting the drive unit, and an arm suspending a wire which connects the force measurement sensor structure and the drive unit, wherein the first and second elastic members can apply a load to the intermediate element in one dimensional direction, and linear potentiometer detects a force applied to the intermediate element, and the control unit controls the drive unit depending on the force applied to the intermediate element.

14 Claims, 27 Drawing Sheets

(51) Int. Cl.
| | |
|---|---|
| A63B 71/00 | (2006.01) |
| A61H 1/00 | (2006.01) |
| A61H 1/02 | (2006.01) |
| A61H 5/00 | (2006.01) |
| A61F 5/01 | (2006.01) |
| G01L 1/04 | (2006.01) |
| G01L 5/00 | (2006.01) |
| A61B 5/22 | (2006.01) |
| A63B 24/00 | (2006.01) |
| G01L 5/10 | (2006.01) |

(52) U.S. Cl.
CPC .......... *A63B 21/153* (2013.01); *A63B 21/4035* (2015.10); *A63B 21/4043* (2015.10); *A63B 24/0062* (2013.01); *A63B 24/0087* (2013.01); *G01L 1/04* (2013.01); *G01L 1/042* (2013.01); *G01L 5/00* (2013.01); *G01L 5/103* (2013.01); *A61H 1/0237* (2013.01); *A61H 1/0274* (2013.01); *A61H 2201/149* (2013.01); *A61H 2201/164* (2013.01); *A61H 2201/165* (2013.01); *A61H 2201/1635* (2013.01); *A61H 2201/1664* (2013.01); *A61H 2201/5061* (2013.01); *A63B 2024/0068* (2013.01); *A63B 2024/0093* (2013.01); *A63B 2220/10* (2013.01); *A63B 2220/51* (2013.01)

(56) References Cited

U.S. PATENT DOCUMENTS

| | | |
|---|---|---|
| 2006/0229164 A1* | 10/2006 | Einav ............... A63B 21/00 482/9 |
| 2006/0276728 A1 | 12/2006 | Ashihara et al. |
| 2008/0154165 A1 | 6/2008 | Ashihara et al. |
| 2008/0161937 A1 | 7/2008 | Sankai |
| 2009/0276058 A1 | 11/2009 | Ueda et al. |
| 2011/0004322 A1 | 1/2011 | Sankai |
| 2011/0266323 A1 | 11/2011 | Kazerooni et al. |

FOREIGN PATENT DOCUMENTS

| | | |
|---|---|---|
| EP | 1 842 486 | 10/2007 |
| JP | 55-101836 | 8/1980 |
| JP | 3-55541 | 5/1991 |
| JP | 2005-501643 | 1/2005 |
| JP | 2005-220856 | 8/2005 |
| JP | 2006-187348 | 7/2006 |
| JP | 2006-204426 | 8/2006 |
| JP | 2006-334200 | 12/2006 |
| JP | 2008-12358 | 1/2008 |
| JP | 2010-75548 | 4/2010 |
| JP | 2011-251057 | 12/2011 |
| WO | 2007/043308 | 4/2007 |
| WO | 2010/101595 | 9/2010 |

OTHER PUBLICATIONS

International Search Report issued Aug. 13, 2013 in International (PCT) Application No. PCT/JP2013/003974.

International Search Report issued Aug. 13, 2013 in International (PCT) Application No. PCT/JP2013/003975.

International Preliminary Report on Patentability and Written Opinion of the International Searching Authority issued Jan. 15, 2015 in International (PCT) Application No. PCT/JP2013/003973.

International Preliminary Report on Patentability and Written Opinion of the International Searching Authority issued Jan. 15, 2015 in International (PCT) Application No. PCT/JP2013/003974.

International Preliminary Report on Patentability and Written Opinion of the International Searching Authority issued Jan. 15, 2015 in International (PCT) Application No. PCT/JP2013/003975.

* cited by examiner

SUPPORT DEVICE, OPERATION SUPPORT DEVICE, AND MUSCLE STRENGTH TRAINING SUPPORT DEVICE

BACKGROUND

1. Technical Field

This disclosure relates to a support device, a muscle strength training support device and an operation support device which support muscles while measuring a force in a transition state.

2. Related Art

Conventionally, an operation support device which supports an operation of a human body has been developed, as shown in WO 2007/043308 and Japanese Patent Laid-open Publication No. 2008-12358. In this operation support device, a sensor which detects the movement of a muscle is used. However, attaching the sensor on the muscle may be difficult.

On the other hand, as a typical method of measuring a force, for example, there is known a method which measures a change in electric resistance by a strain gauge, calculates a strain based on the measured electric resistance, and measures a force applied to a muscle. Also, there is known a method which measures a piezoelectric effect by making use of a strain and measures a force applied to a muscle and the like.

SUMMARY

Among dynamic forces, a human force is not a fixed force. That is, with respect to a human force, the force applied at an initial stage is large, and the force becomes smaller thereafter compared to the force at an initial stage. The direction of the force applied in a later stage may change from the direction of the force applied at the initial stage. To support an operation conducted using a human force, it is necessary to measure a force generated in a later stage rather than a force generated in an initial stage.

However, in such a case, a force sensor which uses a strain gauge or a force sensor which makes use of a piezoelectric effect detects a large force in an initial stage and hence, there exists a drawback that the force sensor detects a force having a magnitude and a direction different from a magnitude and a direction of a force in a later stage. When a large force in an initial stage is measured, a force supplied for supporting an operation becomes excessively large, thus giving rise to a case where an operation support device performs an unpredictable motion. Further, when a force in an initial stage and a force in a later stage differ from each other in direction, there exists a drawback that operation supporting directions become completely opposite.

Accordingly, it is an object of this disclosure to provide a support device which can, in the case where the support device supports a human force which is not a fixed force and is decreased in a later stage compared to an initial stage, support a human force by measuring not a force in the initial stage but a force in the later stage.

In one general aspect, the techniques disclosed here feature: a support device comprising:
a force measurement sensor structure comprising: first and second elastic members; and an intermediate element supported between the first and second elastic members;
a drive unit which is configured to vary a load applied to the intermediate element from the first and second elastic members of the force measurement sensor structure;
a control unit which is configured to control the drive unit; and a wearable unit which a user wears on user's body;
wherein the force measurement sensor structure includes:
a shaft having a first end section and a second end section;
the intermediate element movably provided between the first end section and the second end section along the shaft;
the first elastic member provided between the first end section and the intermediate element along the shaft;
the second elastic member provided between the second end section and the intermediate element along the shaft;
a linear potentiometer connected to the intermediate element and configured to detect a position of the intermediate element in one dimensional direction along the shaft; and
a gripping unit connected to the intermediate element and configured to transmit a force to the intermediate element in an interlocking manner with a movement of an upper limb or a lower limb of the user,
the wearable unit includes:
a front frame provided on a front side of the user;
a rear frame connected to the front frame, provided on a rear side of the user, and supporting the drive unit; and
an arm attached on the front frame, the arm suspending a wire which connects the force measurement sensor structure and the drive unit to each other,
wherein the first and second elastic members are configured to support the intermediate element, are capable of applying a load to the intermediate element in directions opposite to each other in one dimensional direction along the shaft,
the linear potentiometer detects a position of the intermediate element in one dimensional direction along the shaft to measure a force applied to the intermediate element, and
the control unit is configured to control the drive unit depending on the measured force applied to the intermediate element.

The above-mentioned general and specific modes may be realized as an operation support device and a muscle strength training support device which use the above-mentioned support device.

According to the support device of this disclosure, in the case where a support is performed by measuring a force which becomes smaller in a later stage compared to an initial stage, the support can be performed by measuring not the force in the initial stage but the force in the later stage.

DETAILED DESCRIPTION

Figure 1:
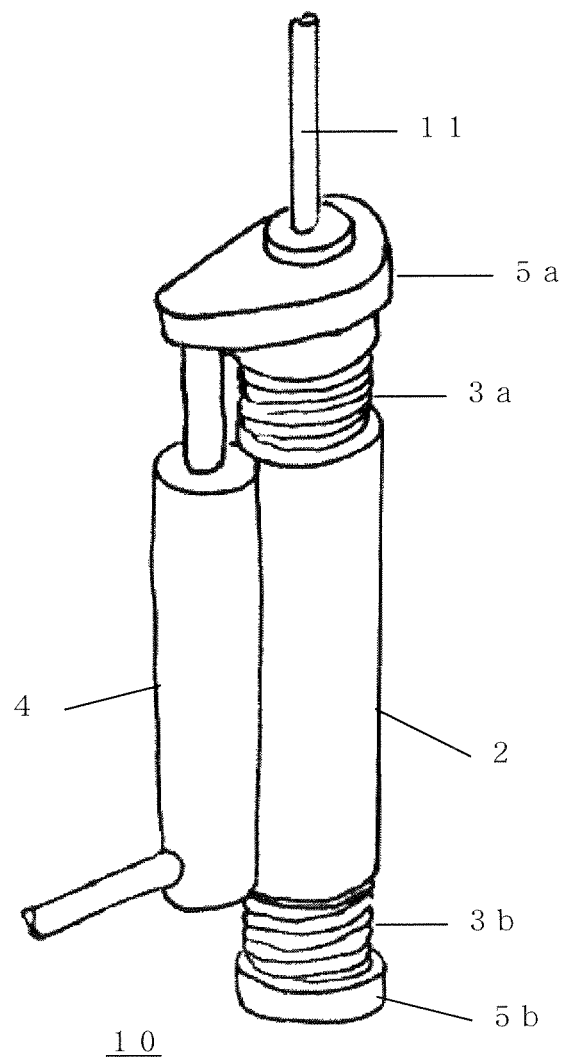
FIG. 1 is a perspective view showing the constitution of a force measurement sensor structure according to a first embodiment of this disclosure.

As a support device of a first aspect, a support device including:

a force measurement sensor structure including: first and second elastic members; and an intermediate element supported between the first and second elastic members;

a drive unit which is configured to vary a load applied to the intermediate element from the first and second elastic members of the force measurement sensor structure;

a control unit which is configured to control the drive unit; and a wearable unit which a user wears on user's body;

wherein the force measurement sensor structure includes:

a shaft having a first end section and a second end section;

the intermediate element movably provided between the first end section and the second end section along the shaft;

the first elastic member provided between the first end section and the intermediate element along the shaft;

the second elastic member provided between the second end section and the intermediate element along the shaft;

a linear potentiometer connected to the intermediate element and configured to detect a position of the intermediate element in one dimensional direction along the shaft; and a gripping unit connected to the intermediate element and configured to transmit a force to the intermediate element in an interlocking manner with a movement of an upper limb or a lower limb of the user, the wearable unit includes:

a front frame provided on a front side of the user;

a rear frame connected to the front frame, provided on a rear side of the user, and supporting the drive unit; and an arm attached on the front frame, the arm suspending a wire which connects the force measurement sensor structure and the drive unit to each other, wherein the first and second elastic members are configured to support the intermediate element, are capable of applying a load to the intermediate element in directions opposite to each other in one dimensional direction along the shaft, the linear potentiometer detects a position of the intermediate element in one dimensional direction along the shaft to measure a force applied to the intermediate element, and the control unit is configured to control the drive unit depending on the measured force applied to the intermediate element.

Further, as a support device of a second aspect, in the first aspect, the drive unit is configured to vary at least one of a magnitude of a load applied to the intermediate element from the first elastic member and the second elastic member and a direction of the load.

Further, as a support device of a third aspect, in the first aspect, the wearable unit includes a rear frame open/close mechanism which is configured to open or close the rear frame.

Further, as a support device of a fourth aspect, in the third aspect, the rear frame open/close mechanism is constituted of a rotatable hinge portion which connects the front frame and the rear frame, and is configured to open or close the rear frame upward using the hinge portion as a fulcrum.

Further, as a support device of a fifth aspect, in the fourth aspect, the rear frame open/close mechanism connects the rear frame and the arm to each other, includes a damper which imparts a buffer action to the movement of the rear frame and the movement of the arm, and is configured to buffer an open/close operation of the rear frame by the damper in opening or closing the rear frame.

Further, as a support device of a sixth aspect, in the third aspect, the rear frame open/close mechanism is configured to open or close at least a portion of the rear frame sideward.

Further, as a support device of a seventh aspect, in the third aspect, the rear frame open/close mechanism is configured to open or close at least a portion of the front frame upward.

Further, as a support device of a eighth aspect, in the first aspect, further including:

a slide rail provided on the front frame; and a slide frame arranged on the slide rail and relatively movable relative to the front frame by the slide rail.

Further, as a support device of a ninth aspect, in the first aspect, further including: a side bar connecting the front frame and the rear frame along a side portion of a user such that a width between the front frame and the rear frame is variable.

Further, as a support device of a tenth aspect, in the first aspect, the arm is arranged at respective portions of the front frame corresponding to both shoulders of the user, respectively.

Further, as a support device of a eleventh aspect, in the first aspect, further including: a shoulder belt for supporting the wearable unit by being suspended from a shoulder of the user.

Further, as a support device of a twelfth aspect, in the first aspect, the first and second elastic members are each constituted of one or more kinds of members selected from a group consisting of spring, rubber, air and the like.

Further, as a operation support device of a thirteenth aspect, an operation support device including the support device according to the first aspect, wherein the control unit is configured to support a movement of an upper limb or a lower limb of the user by controlling the drive unit such that a measured force applied to the intermediate element is decreased depending on a movement of an upper limb or a lower limb of the user.

Further, as a muscle strength training support device of a fourteenth aspect, a muscle strength training support device including the support device according to first aspect, wherein the control unit is configured to support muscle strength training of an upper limb or a lower limb of the user by controlling the drive unit such that a predetermined force is applied to the intermediate element depending on a movement of an upper limb or a lower limb of the user.

Hereinafter, a support device, an operation support device and a muscle strength training support device according to the present invention are explained with reference to attached drawings. In the drawings, substantially identical members are given same symbols.

First Embodiment

Force Measurement Sensor Structure

Figure 2:
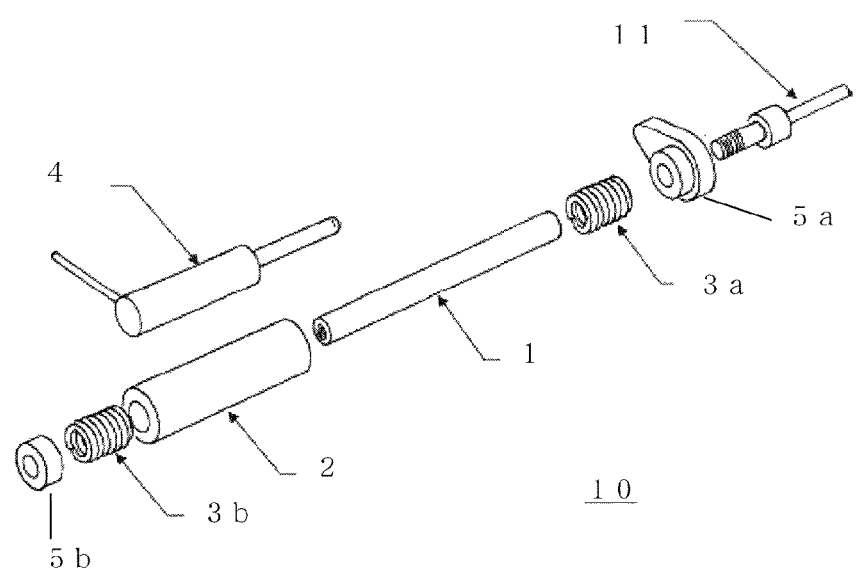
FIG. 2 is an exploded perspective view of the force measurement sensor structure shown in FIG. 1.

FIG. 1 is a schematic perspective view showing the constitution of the force measurement sensor structure 10 according to a first embodiment. FIG. 2 is an exploded perspective view of the force measurement sensor structure 10 shown in FIG. 1.

The force measurement sensor structure 10 includes: a shaft 1 having a first end section 5a and a second end section 5b; an intermediate element 2 movably provided between the first end section 5a and the second end section 5b along the shaft 1; a first elastic member 3a provided between the first end section 5a and the intermediate element 2 along the shaft 1; a second elastic member 3b provided between the second end section 5b and the intermediate element 2 along the shaft 1; and a linear potentiometer 4 connected to the intermediate element 2 and detecting the position of the intermediate element 2 in one dimensional direction along the shaft 1. The first and second elastic members 3a, 3b are configured to apply a load to the intermediate element 2 in the directions opposite to each other in one dimensional direction along the shaft 1 while supporting the intermediate element 2. In the force measurement sensor structure 10, the linear potentiometer 4 detects the position of the intermediate element 2 in one dimensional direction along the shaft 1 to measure a force applied to the intermediate element 2.

Hereinafter, the members which constitute the force measurement sensor structure 10 are explained.

<Shaft>

The shaft 1 is provided for supporting the intermediate element 2 and the first and second elastic members 3a, 3b. The shaft 1 defines the movement of the intermediate element 2 between both end sections 5a, 5b thereof. In FIG. 1 and FIG. 2, the intermediate element 2 and the first and second elastic members 3a, 3b are provided such that the shaft 1 passes through these members. However, the shaft 1 is not limited to such a structure and, for example, the shaft 1 may be configured to pass through a groove formed on the side surface of the intermediate element 2. As a material for the shaft 1, any material can be used provided that the material is usually used in the force measurement such as iron, stainless steel, aluminum, wood or bamboo, for example.

<Intermediate Element>

The intermediate element 2 is movably disposed between both end sections 5a, 5b, thereof along the shaft 1. As a material for the intermediate element 2, any material can be used provided that the material is usually used in the force measurement such as iron, stainless steel, aluminum, wood or bamboo.

<First and Second Elastic Members>

The first elastic member 3a is provided between the first end section 5a and the intermediate element 2 along the shaft 1. The second elastic member 3b is provided between the second end section 5b and the intermediate element 2 along the shaft 1. The first and second elastic members 3a, 3b are provided at both ends of the intermediate element 2 thus supporting the intermediate element 2. The first and second elastic members 3a, 3b are configured to support the intermediate element 2 and to apply a load to the intermediate element 2 in directions opposite to each other in one dimensional direction along the shaft 1.

<Linear Potentiometer>

The linear potentiometer 4 is connected to the intermediate element 2, and detects the position of intermediate element 2 in one dimensional direction along the shaft 1. It is sufficient that the linear potentiometer 4 can detect the position of the intermediate element 2 in one dimensional direction, and the linear potentiometer 4 which is usually used can be used. In FIG. 1 and FIG. 2, one end section of the linear potentiometer 4 is fixed to an end section on a first elastic member 3a side. However, fixing of the linear potentiometer 4 is not limited to such a case, and the linear potentiometer 4 may be fixed to an end section on a second elastic member 3b side.

(Modification)

Figure 3:
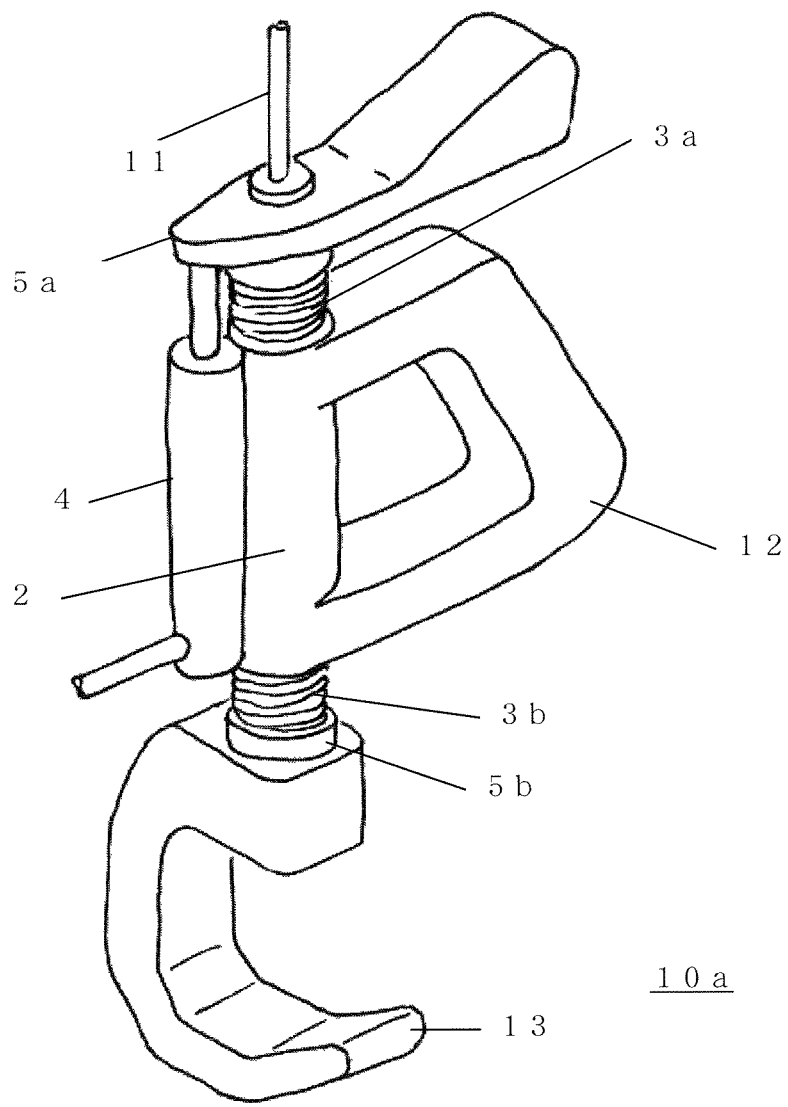
FIG. 3 is a perspective view showing the constitution of a modification of the force measurement sensor structure according to the first embodiment of this disclosure.

FIG. 3 is a perspective view showing the constitution of the force measurement sensor structure 10a according to a modification of the first embodiment of this disclosure. In comparison, the force measurement sensor structure 10a according to the modification differs from force measurement sensor structure 10 shown in FIG. 1 with respect to a point where a gripping unit (grip) 12 is provided to an intermediate element 2. A user can easily apply a force to the intermediate element 2 by gripping the gripping unit 12 with either hand. In FIG. 3, the gripping unit 12 has a grip shape suitable for gripping with a hand. However, the gripping unit 12 is not limited to such a structure and, for example, the gripping unit 12 may be formed into a pedal shape so that a user can step on the gripping unit 12. It is sufficient that the gripping unit 12 be configured to apply a force to the intermediate element 2 in an interlocking manner with the movement of an upper limb (arm) or a lower limb (leg). Further, the force measurement sensor structure 10a according to the modification of the first embodiment of this disclosure has a hook 13 at one end thereof. An object to be moved can be suspended from the hook 13.

Figure 4A:
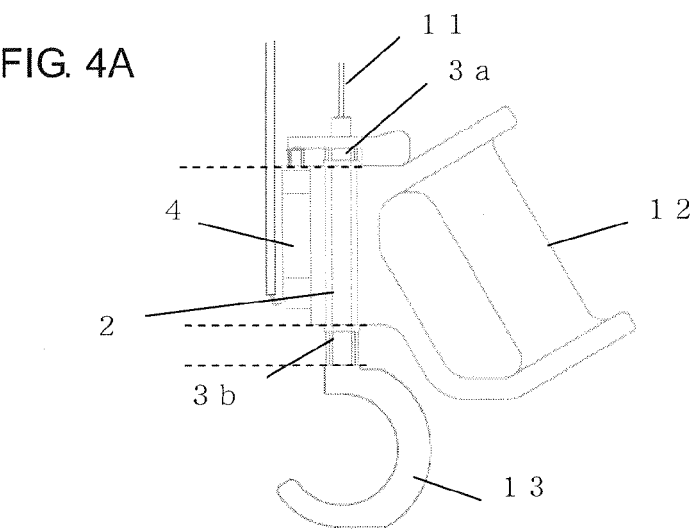
FIG. 4A is a front view of the force measurement sensor structures 10, 10a shown in FIG. 1 and FIG. 3, and shows a position of an intermediate element when a force is applied to the intermediate element in the upward (+) direction, so that the intermediate element is moved upwardly.
Figure 4B:
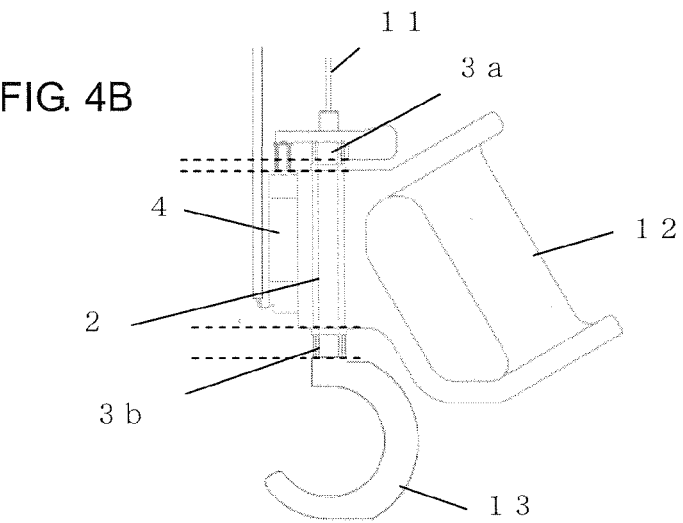
FIG. 4B is a front view of the force measurement sensor structures 10, 10a shown in FIG. 1 and FIG. 3, and shows the position of the intermediate element when a force is not applied to the intermediate element.
Figure 4C:
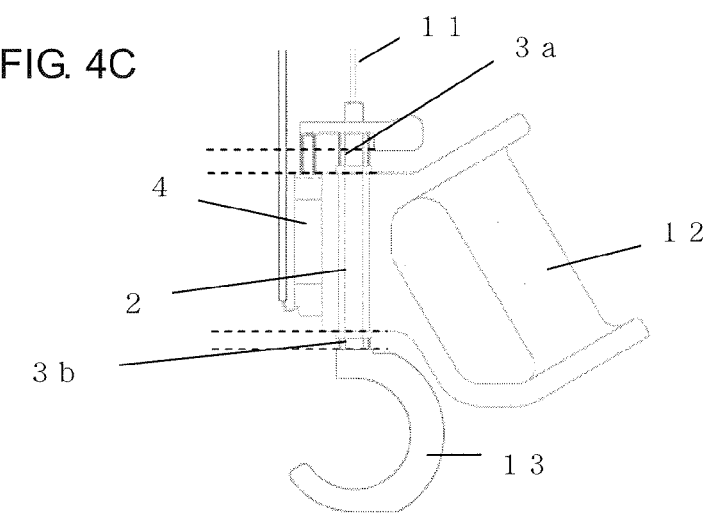
FIG. 4C is a front view of the force measurement sensor structures 10, 10a shown in FIG. 1 and FIG. 3, and shows the position of the intermediate element when a force is applied to the intermediate element in the downward (−) direction, so that the intermediate element is moved downwardly.

FIG. 4A is a front view, in the force measurement sensor structure 10, 10a shown in FIG. 1 and FIG. 3, showing the position of the intermediate element 2 when the force in the upward (+) direction is applied to the intermediate element 2 so that the intermediate element 2 is moved upwardly. FIG. 4B shows a front view showing the position of the intermediate element 2 when a force is not applied to the intermediate element 2. FIG. 4C is a front view showing the position of the intermediate element 2 when a force is applied to the intermediate element 2 in the downward (−) direction so that the intermediate element 2 is moved downwardly.

As shown in FIG. 4A, when the intermediate element 2 is in the upward position, the first elastic member 3a is compressed and, at the same time, the second elastic member 3b is extended and hence, a downward load is applied to the intermediate element 2 from the first and second elastic members 3a, 3b. On the other hand, as shown in FIG. 4C, when the intermediate element 2 is at the downward position, the first elastic member 3a is extended, and at the same time, the second elastic member 3b is compressed and hence, an upward load is applied to the intermediate element 2 from the first and second elastic members 3a, 3b. In these force measurement sensor structures 10, 10a, the linear potentiometer 4 detects the position of the intermediate element 2 in one dimensional direction along the shaft 1 and measures a force applied to the intermediate element 2. For example, when the position of the intermediate element 2 is in the upward direction, it is understood that a downward load is applied to the intermediate element 2. On the other hand, when the position of the intermediate element 2 is in the downward direction, it is understood that an upward load is applied to the intermediate element 2.

<Load Control Device>

Figure 5:
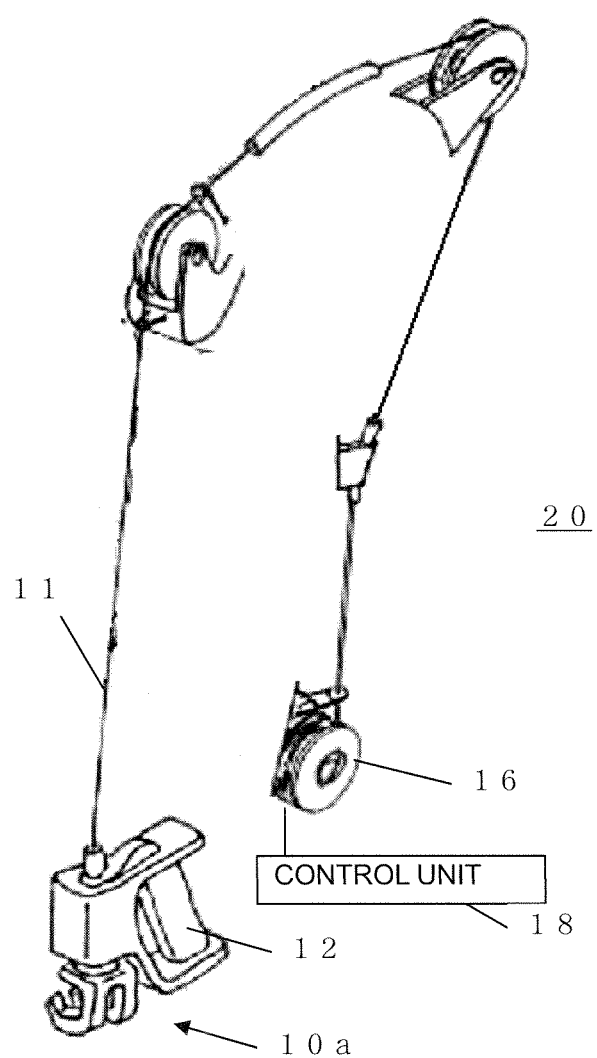
FIG. 5 is a perspective view showing the constitution of a load control device according to the first embodiment of this disclosure.
Figure 6:
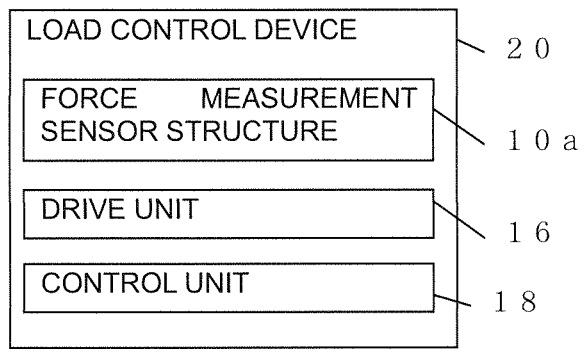
FIG. 6 is a block diagram showing the functional constitution of the load control device shown in FIG. 5.

FIG. 5 is a perspective view showing the constitution of a load control device 20 according to the first embodiment. FIG. 6 is a block diagram showing the functional constitution of the load control device 20 shown in FIG. 5.

As shown in FIG. 5 and FIG. 6, the load control device 20 includes: the force measurement sensor structure 10a, a wire 11 fixed to an upper portion of the force measurement sensor structure 10a; a motor (drive unit) 16 which reels in or reels out the wire 11; and a control unit 18 which controls the motor (drive unit) 16. The wire 11 is fixed to the upper end of the force measurement sensor structure 10a and hence, by pulling the wire 11 upward by reeling in the wire 11 along with driving of the motor (drive unit) 16 or releasing the wire 11 by reversely rotating the motor 16, a load applied to the intermediate element 2 from the first and second elastic members 3a, 3b can be varied. The control unit 18 controls the drive unit 16 depending on a measured force applied to the intermediate element 2.

Hereinafter, the members which constitute the load control device 20 are explained.

<Drive Unit>

As the drive unit 16, for example, it is possible to use a motor or the like which can wind the wire 11 or can release the wire 11 by being rotated in the reversed direction. The constitution of the drive unit 16 is not limited to a motor, and any means can be used provided that the means can change a load applied to the intermediate element 2 from the first and second elastic members 3a, 3b. For example, in the above-mentioned motor 16, the upper end to which the first elastic member 3a and the second elastic member 3b are fixed is moved upward or downward by pulling the wire 11. However, a load applied to the intermediate element 2 from the first elastic member 3a and the second elastic member 3b may be varied by changing the relative position of the intermediate element 2 with respect to the first elastic member 3a and the second elastic member 3b upward or downward.

<Control Unit>

Figure 7:
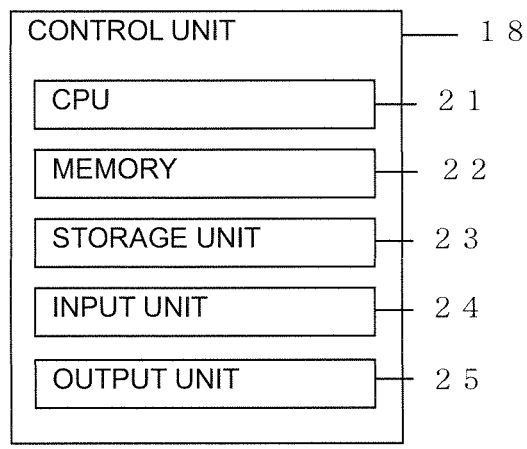
FIG. 7 is a block diagram showing a physical constitutional example of a control unit shown in FIG. 6.
Figure 8:
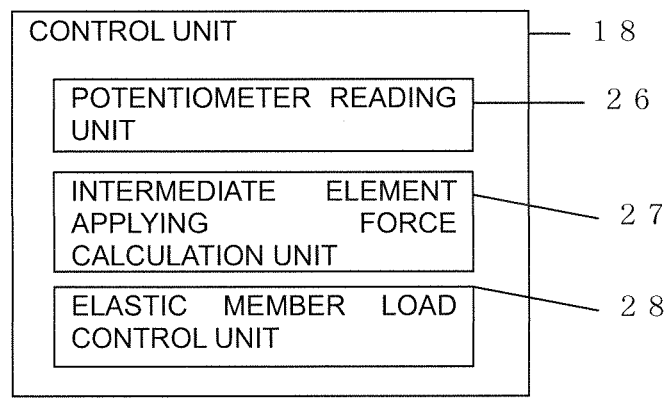
FIG. 8 is a block diagram showing the functional constitutional example of the control unit shown in FIG. 6.

FIG. 7 is a block diagram showing a physical constitutional example of the control unit 18 in FIG. 6. FIG. 8 is a block diagram showing a functional constitutional example of the control unit 18 in FIG. 6.

The control unit 18 may be, for example, as shown in FIG. 7, realized by a personal computer which includes: a CPU 21; a memory 22; a storage unit 23; an input unit 24; an output unit 25 and the like. The functional constitution of the control unit 18 may include: as shown in FIG. 8, a potentiometer reading unit 26 which reads a value of a potentiometer; an intermediate element applied force calculation unit 27 which calculates a force applied to the intermediate element 2; and an elastic member load control unit 28 which controls a load applied to the intermediate element 2 from the first and second elastic members 3a, 3b.

<Support Device (Operation Support Device and Muscle Strength Training Support Device)>

Figure 9:
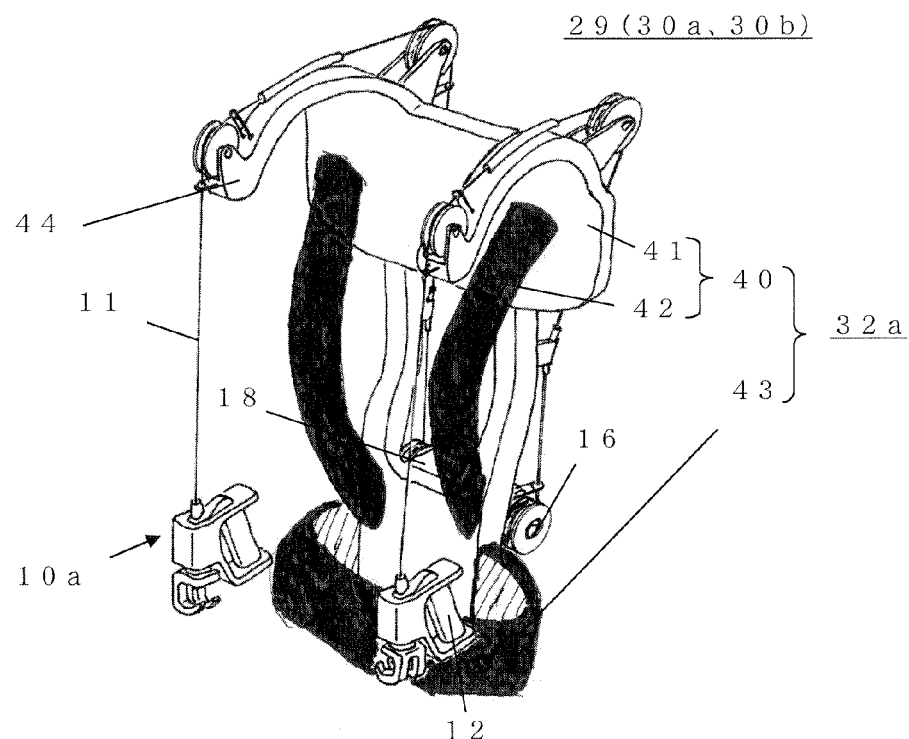
FIG. 9 is a perspective view showing the constitution of an operation support device/a muscle strength training support device according to the first embodiment of this disclosure.
Figure 10:
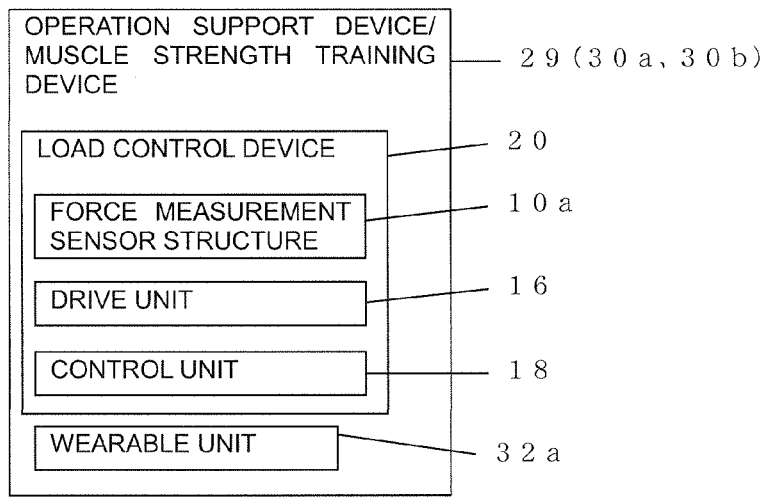
FIG. 10 is a block diagram showing the functional constitution of the operation support device/muscle strength training support device shown in FIG. 9.

FIG. 9 is a schematic perspective view showing the constitution of a support device 29 (an operation support device 30a and a muscle strength training support device 30b) according to the first embodiment. FIG. 10 is a block diagram showing a functional constitution of the support device 29 (operation support device 30a/muscle strength training support device 30b) shown in FIG. 9. The operation support device 30a and the muscle strength training support device 30b are collectively referred to as the support device 29.

The support device 29 (the operation support device 30a and the muscle strength training support device 30b) includes the above-mentioned load control device 20 and a body wearable unit 32a. The force measurement sensor structure 10a of the load control device 20 includes the gripping unit 12. The gripping unit 12 is connected to the intermediate element 2 of the force measurement sensor structure 10a. A force is transmitted to the intermediate element 2 in an interlocking manner with the movement of an upper limb or a lower limb of a user. Specifically, the gripping unit 12 is provided for enabling the user to grip the gripping unit 12 thus easily applying a force to the force measurement sensor structure 10a. Although the gripping unit 12 is formed into a shape so that a user can grip the gripping unit 12 with either hand in the example in FIG. 9, the gripping unit 12 is not limited to the example in FIG. 9, and the gripping unit 12 may be fixed to an upper limb or a lower limb of a user such that the gripping unit 12 can be moved in an interlocking manner with the upper limb or the lower limb of the user. Further, the force measurement sensor structure 10a may be made more easily wearable by the body wearable unit 32a. The body wearable unit 32a is not indispensable for the constitution of the support device 29 (the operation support device 30a and the muscle strength training support device 30b).

(Body Wearable Unit 32a: Backpack Type Wearable Unit)

The body wearable unit 32a is explained with reference to FIG. 9. The body wearable unit 32a includes: a back rest portion 41 and shoulder belts 42 which are suspended from shoulder portions of a user and constitutes a main frame 40 to which the drive unit 16 is fixed; a waist belt 43 used for mounting the main frame 40 on an abdomen of a user; and arms 44 which are attached on the main frame 40 and suspend wires 11 for connecting the force measurement sensor structure 10a and the drive units 16 to each other. The back rest portion 41 is formed using the metal or resin. The shoulder belts 42 and the waist belts 43 are formed using metal, resin, natural fiber or the like. The arms 44, the force measurement sensor structure 10a and the drive unit 16 are provided in two sets respectively in FIG. 9. However, the body wearable unit 32a is not limited to such a constitution, and the arms 44, the force measurement sensor structure 10a and the drive units 16 may be provided in one sets, three sets or more.

The body wearable unit 32a is of a type where a user passes his arms through the shoulder belts 42 and carries the body wearable unit 32a on his back. That is, the body wearable unit 32a is so-called backpack type wearable unit. The body wearable unit 32a can be formed using an apparel member and hence, can be manufactured at a low cost and can be made light-weighted. Further, the body wearable unit 32a is of a backpack type and hence, the method of wearing the body wearable unit 32a can be intuitively understood very easily. Further, a heavy object such as the motor is provided around a waist and hence, the body wearable unit 32a has an advantage that a burden imposed to the user in a front inclined posture becomes minimal. Further, there is no frame or the like in front of the body of the user and the user can be ensured of a large movable range of arm movement and hence, the body wearable unit 32a has an advantage that body wearable unit 32a exhibits favorable operability, when the user keeps on the support device.

(First Modification: Body Wearable Unit 36: Front Holding Type Wearable Body Unit)

Figure 24:
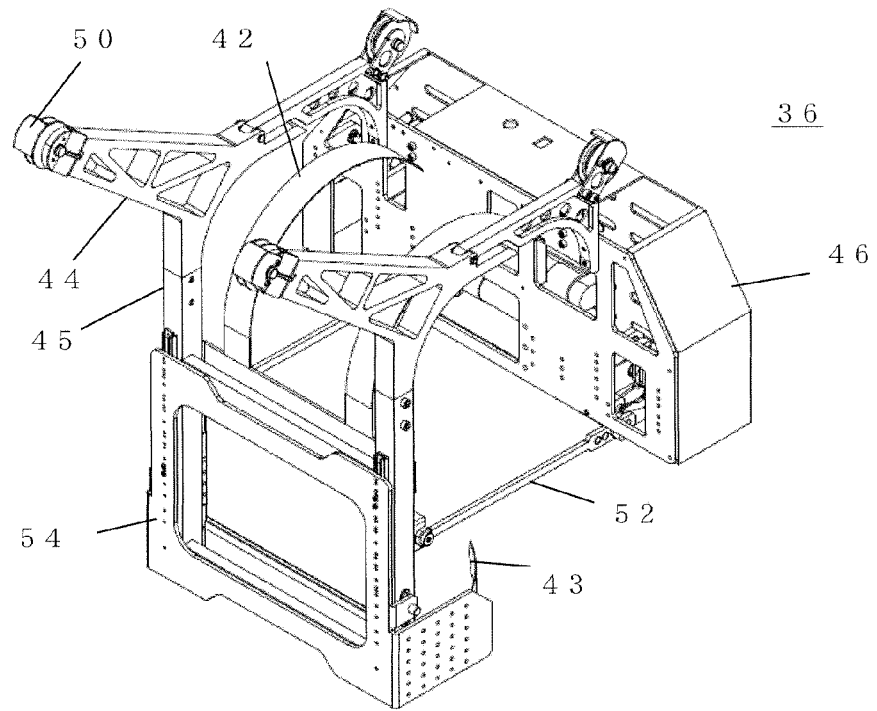
FIG. 24 is a schematic perspective view showing the constitution of a body wearable unit of a first modification used in the support device according to the first embodiment.
Figure 25:
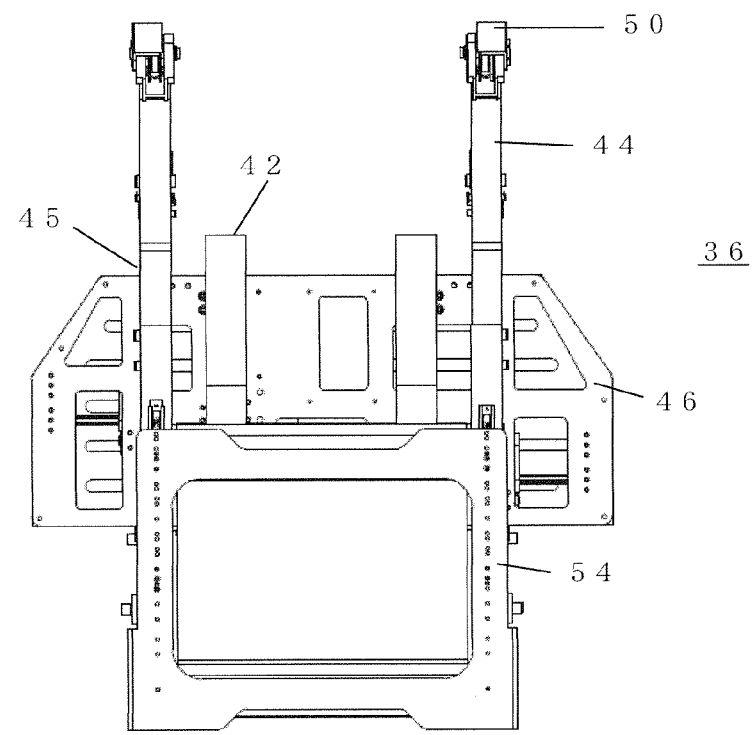
FIG. 25 is a front view of the body wearable unit of the first modification shown in FIG. 24.
Figure 26:
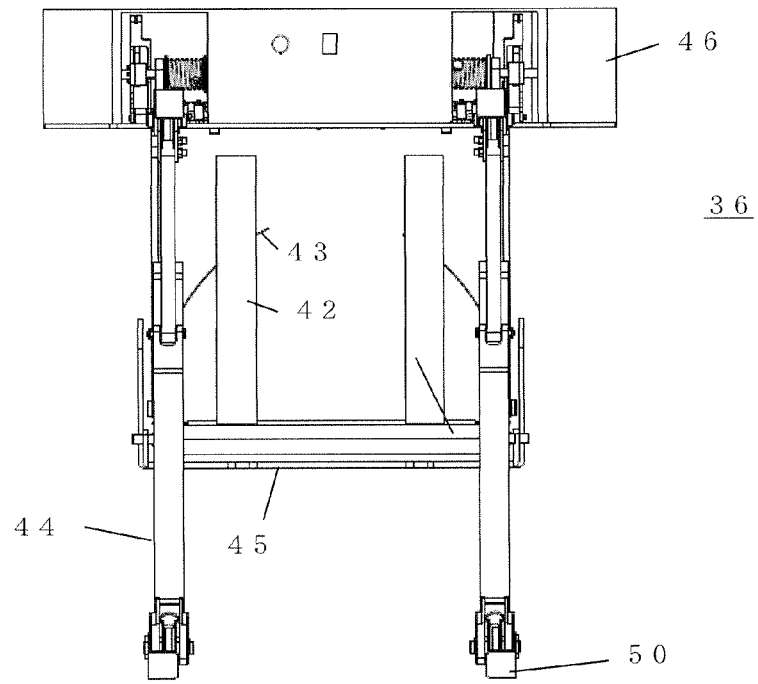
FIG. 26 is a plan view of the body wearable unit of the first modification shown in FIG. 24.
Figure 27:
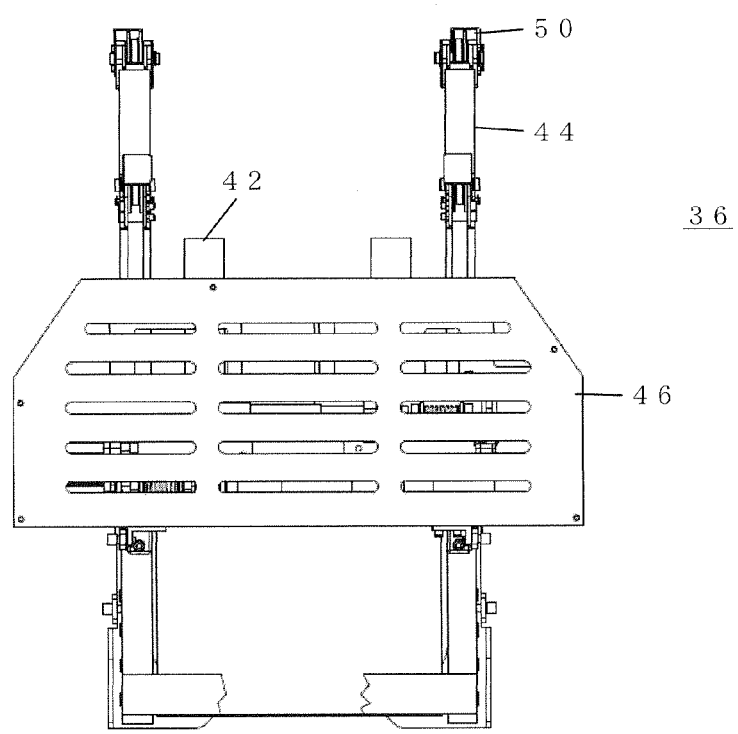
FIG. 27 is a back view of the body wearable unit of the first modification shown in FIG. 24.
Figure 28:
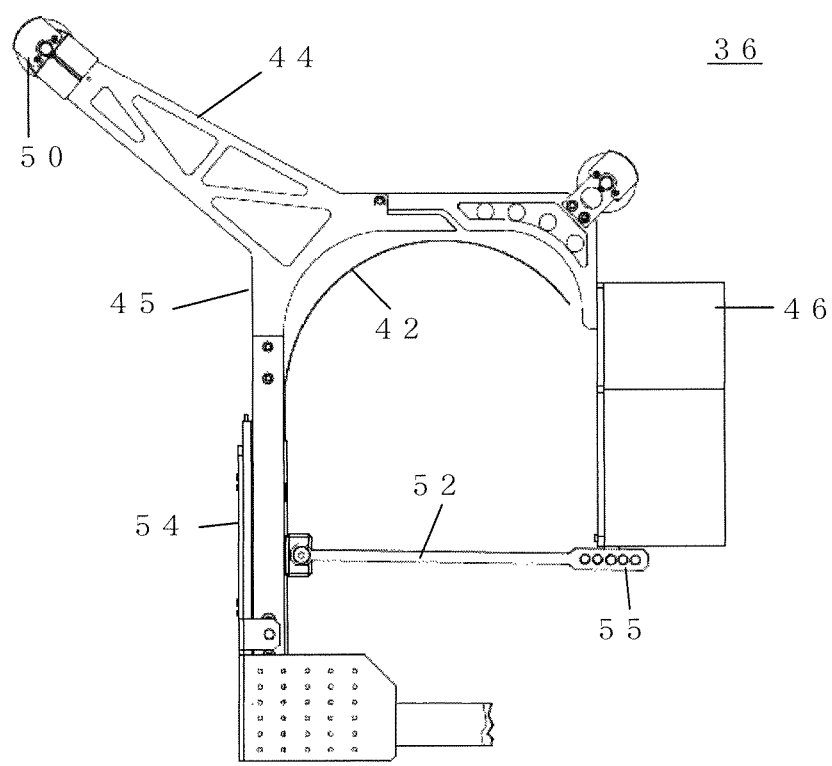
FIG. 28 is a left side view of the body wearable unit of the first modification shown in FIG. 24.

FIG. 24 is a schematic perspective view showing the constitution of a body wearable unit 36 of a first modification used in the support device 29. FIG. 25 is a front view of the body wearable unit 36 of the first modification in FIG. 24. FIG. 26 is a plan view of the body wearable unit 36 of the first modification shown in FIG. 24. FIG. 27 is a back view of the body wearable unit 36 of the first modification shown in FIG. 24. FIG. 28 is a left side view of the body wearable unit 36 of the first modification shown in FIG. 24.

The body wearable unit 36 of the support device 29 shown in FIG. 24 to FIG. 28 differs from the body wearable unit 32a shown in FIG. 9 with respect to a point where the body wearable unit 36 is not a backpack type wearable unit but is a front holding type wearable unit. Specifically, in the body wearable unit 36, the main frame 40 shown FIG. 9 is constituted of: a front frame 45 provided on a front side of a user; and a rear frame 46 connected to the front frame 45 and provided on a rear side of the user. The front frame 45 and the rear frame 46 are formed using metal or resin, and these frames, 45, 46 may be also formed using a material having rigidity. In this modification, the material having rigidity is a material which holds a fixed shape in itself, and is minimally deformed when predetermined load is applied. The front frame 45 and the rear frame 46 may be suitably adjusted in conformity with a body shape of the user. Arms 44 are provided on the front frame 45, and suspend wires which connect the force measurement sensor structure and drive units. The number of arms 44 is not limited to one and may be two or more. For example, the arm 44 may be arranged on portions of the front frame 45 corresponding to both shoulders of a user respectively. The front frame 45 and the rear frame 46 are connected with each other above both shoulders of the user by a hinge portion 51 described later. Side bars 52 which connect the front frame 45 and the rear frame 46 under user's arm may be provided. A roller 50 from which the wire 11 is suspended may be provided on a distal end of the arm 44. The body wearable unit 36 may further includes shoulder belts 42 for supporting the body wearable unit 36 by being suspended from the shoulders of the user. The shoulder belt 42 may be adjustable in the horizontal direction in conformity with a body shape of the user. Due to such a structure, the position of the body wearable unit 36 in the horizontal direction may be adjusted. A waist belt 43 may be provided by fixing the body wearable unit 36 to a waist of a user. Further, a cushion may be arranged on the front frame 45 so as to protect an abdominal part of a user.

The support device 29 which uses the body wearable unit 36 of the first modification has the following advantages. In the support device 29, in FIG. 9, the front frame 45 and the rear frame 46 substantially play the same role as the main frame 40 having rigidity and hence, a user can put on the support device 29 by himself by putting on the support device 29 over his head. Further, a load is supported by the shoulders and a large front surface of the user's body and hence, the load can be distributed whereby the sensation of compression on the body can be largely decreased. A large field of vision can be ensured by extending arms 44 from the front frame 45. The shoulder is used as a fulcrum, the arm 44 is arranged more on the front side than the fulcrum, and a heavy object such as the motor which is the drive unit 16 is arranged on the rear frame 46 more on the rear side than the fulcrum and hence, a load is directly applied to a core of the body from the shoulder, whereby the load (work) holding posture becomes stable, and a moment applied to the body by the load can be reduced.

The body wearable unit 36 of the first modification may have the following three mechanisms. That is, a rear frame open/close mechanism, a slide frame height adjustment mechanism, and a width adjustment mechanism of the front frame and the rear frame.

Figure 29A:
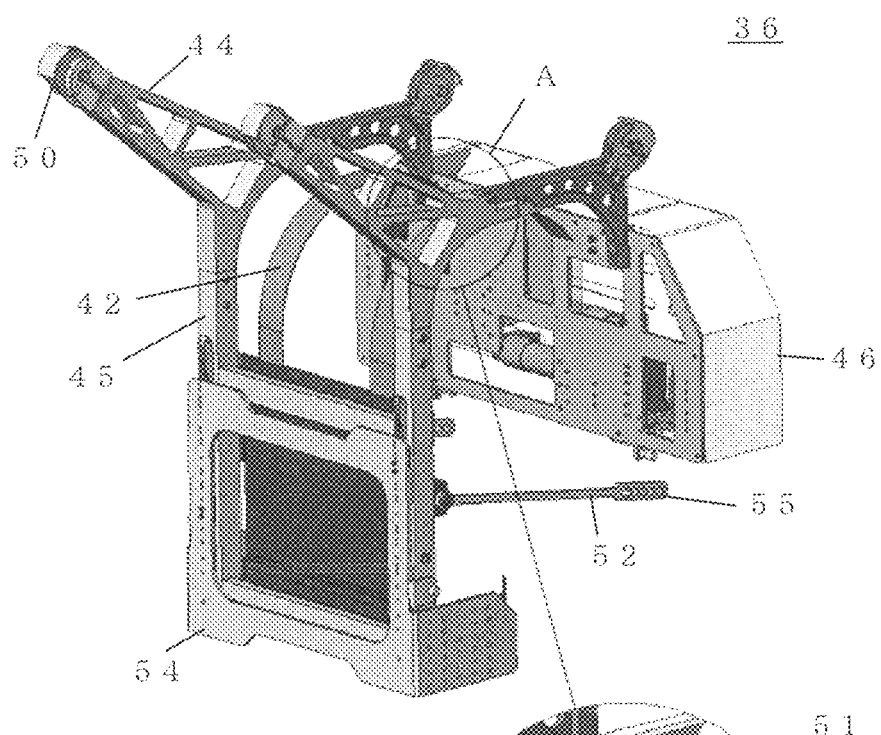
FIG. 29A is a perspective view showing a frame open/close mechanism of the body wearable unit according to the first modification shown in FIG. 24.
Figure 29B:
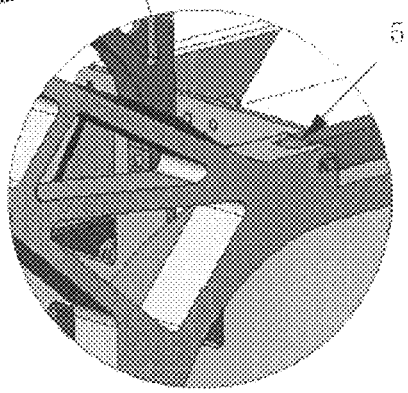
FIG. 29B is an enlarged view showing a portion A of a hinge portion for opening or closing a rear frame.
Figure 30:
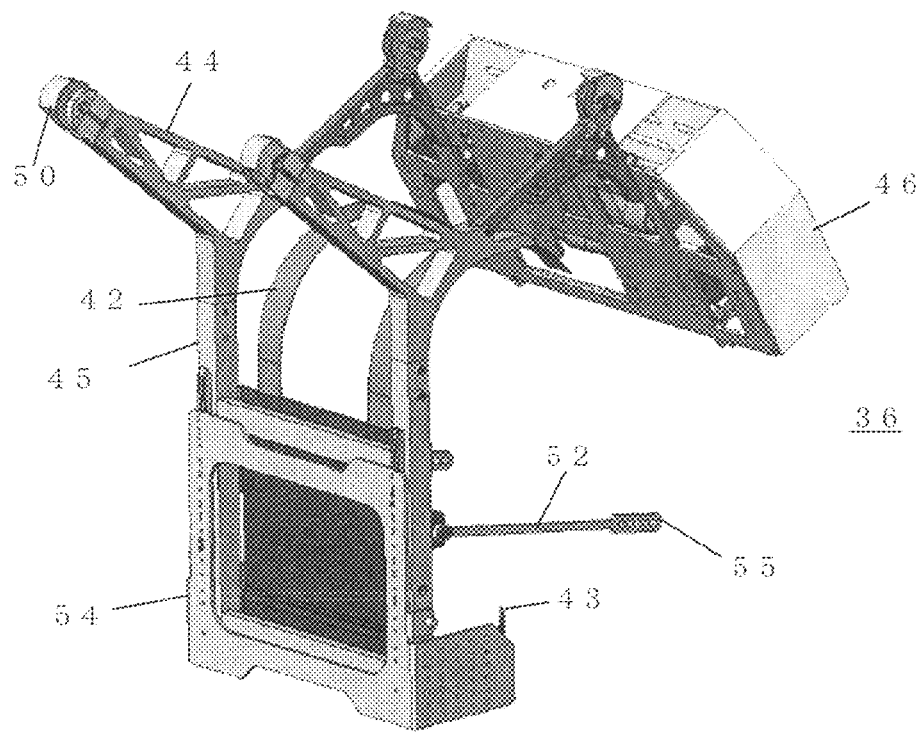
FIG. 30 is a perspective view showing a state where the rear frame of the body wearable unit shown in FIG. 29A is opened upward.

(Rear Frame Open/Close Mechanism) FIG. 29A is a perspective view showing the rear frame open/close mechanism in the body wearable unit 36 of the first modification in FIG. 24. FIG. 29B is an enlarged view showing a portion A of a hinge portion 51 for opening or closing the rear frame 46. FIG. 30 is a perspective view showing a state where the rear frame 46 of the body wearable unit 36 shown in FIG. 29A is opened upwardly. The body wearable unit 36 of the first modification includes a mechanism which opens and closes the rear frame 46. Specifically, the rear frame open/close mechanism is constituted of a rotatable hinge portion 51 which connects the front frame 45 and the rear frame 46 to each other. As shown in FIG. 30, the rear frame 46 can be opened or closed upwardly using the hinge portion as a fulcrum. Due to such a constitution, in the support device using the body wearable unit 36, it is possible to easily cover the body wearable unit 36 from the below.

The rear frame open/close mechanism is not limited to the mechanism which uses the above-mentioned hinge portion 51, and it is sufficient that the rear frame open/close mechanism can open or close the rear frame 46.

[Height Adjustment Mechanism for Slide Frame]

Figure 31:
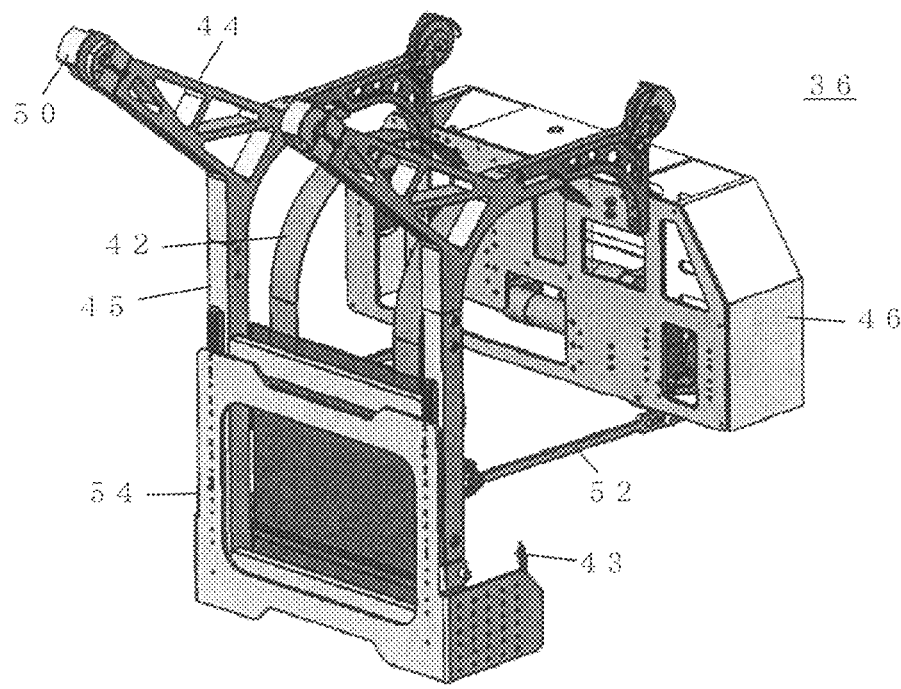
FIG. 31 is a perspective view showing a state where a height of a slide frame is higher than a front frame of the body wearable unit of the first modification shown in FIG. 24.
Figure 32:
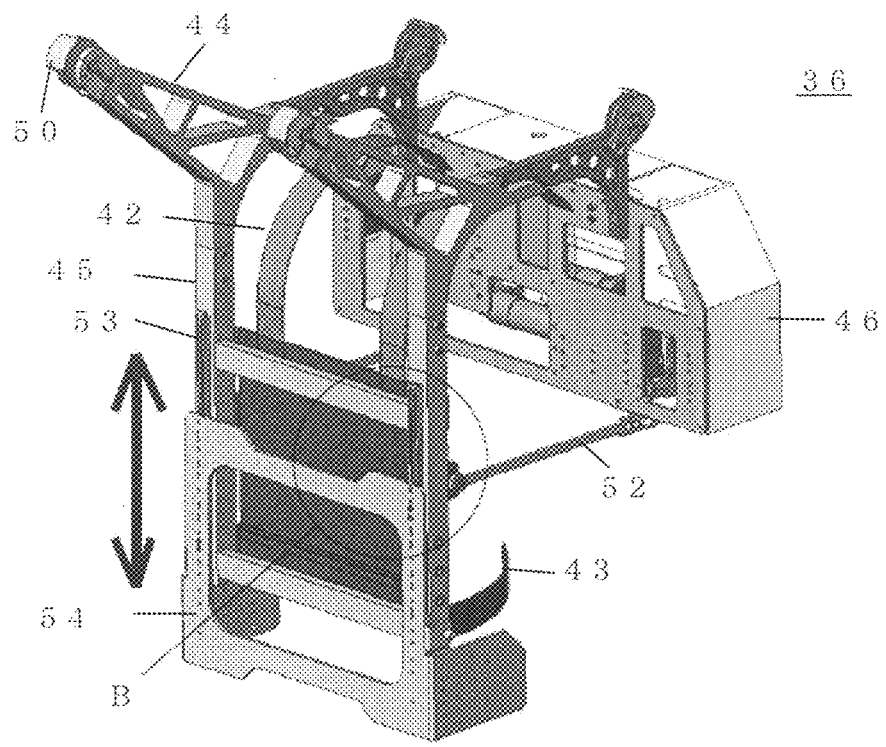
FIG. 32 is a perspective view showing a state where the height of the slide frame is lower than the front frame of the body wearable unit of the first modification shown in FIG. 24.
Figure 33:
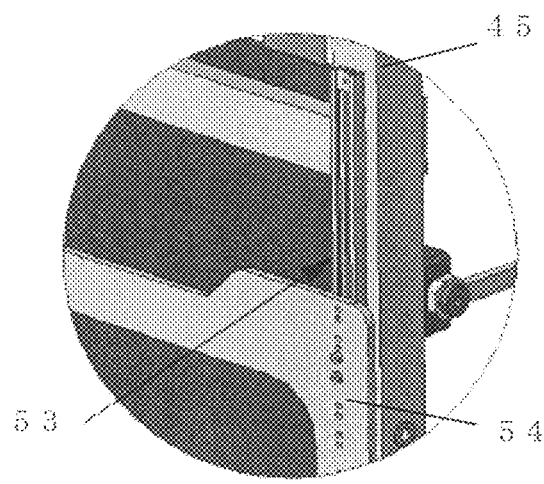
FIG. 33 is an enlarged view of a portion B of a slide rail for adjusting the height of the slide frame with respect to the front frame of the body wearable unit shown in FIG. 32.

FIG. 31 is a perspective view showing a state where a height of a slide frame 54 is higher than the front frame 45 of the body wearable unit 36 of the first modification shown in FIG. 24. FIG. 32 is a perspective view showing a state where the height of the slide frame 54 is lower than the front frame 45 of the body wearable unit 36 of the first modification shown in FIG. 24. FIG. 33 is an enlarged view of a portion B of a slide rail 53 for adjusting the height of the slide frame 54 with respect to the front frame 45 of the body wearable unit 36 of the first modification shown in FIG. 32.

The body wearable unit 36 of the first modification includes slide rails 53 which are provided on the front frame 45 and the slide frame 54 which is arranged on the slide rails 53 and is relatively movable with respect to the front frame 45 by the slide rails 53. Due to such a constitution, the height of the slide frame 54 can be adjusted. For example, the height of the slide frame 54 may be adjusted in conformity with the height of a user. Further, in FIG. 31 and FIG. 32, the waist belt 43 is provided on the front frame 45. The waist belt 43 may be provided on the slide frame 54. In this case, the height of the waist belt 43 can be adjusted by adjusting the height of the slide frame 54.

The height adjustment of the slide frame 54 is not limited to the above-mentioned case where the slide rails 53 are used, and any adjustment is allowable provided that the height of the slide frame 54 can be adjusted.

In FIG. 31 to FIG. 33, the slide rails 53 extending in the vertical direction are provided, and the height of the slide frame 54 is adjusted. However, the adjustment is not limited to the height adjustment and, for example, slide rails extending in the horizontal direction are provided and the horizontal position of the slide frame 54 may be adjusted.

[Width Adjustment Mechanism for Front Frame and Rear Frame]

Figure 34:
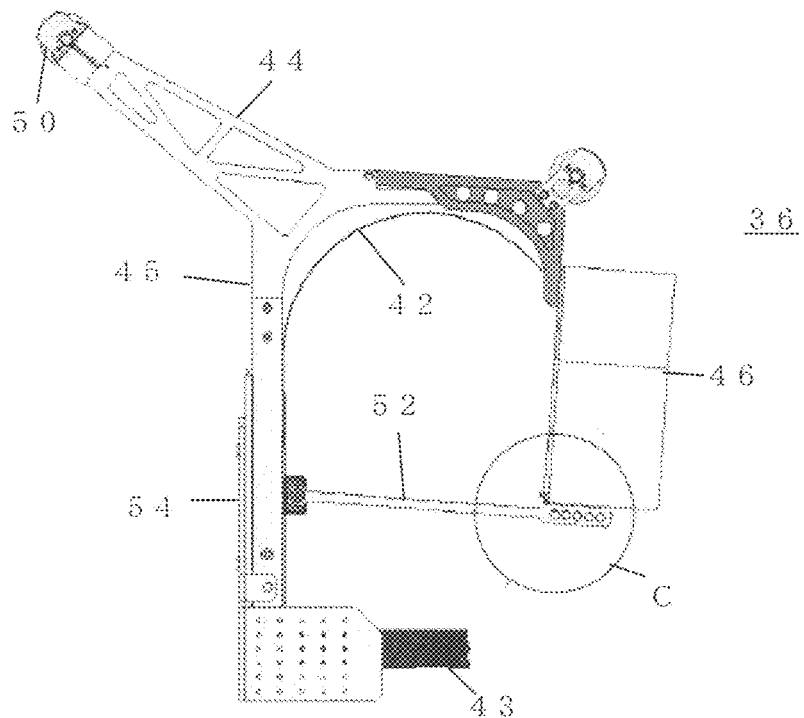
FIG. 34 is a left side view showing a side bar which connects the front frame and a rear frame of the body wearable unit of the first modification shown in FIG. 24 to each other along a side of a user while narrowing a width between the front frame and the rear frame.
Figure 35:
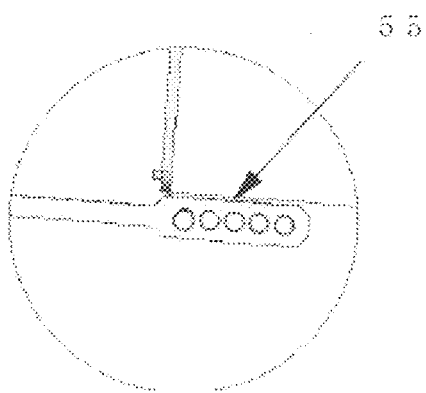
FIG. 35 is an enlarged view of a connection portion C of the side bar which connects the front frame and the rear frame to each other shown in FIG. 34.
Figure 36:
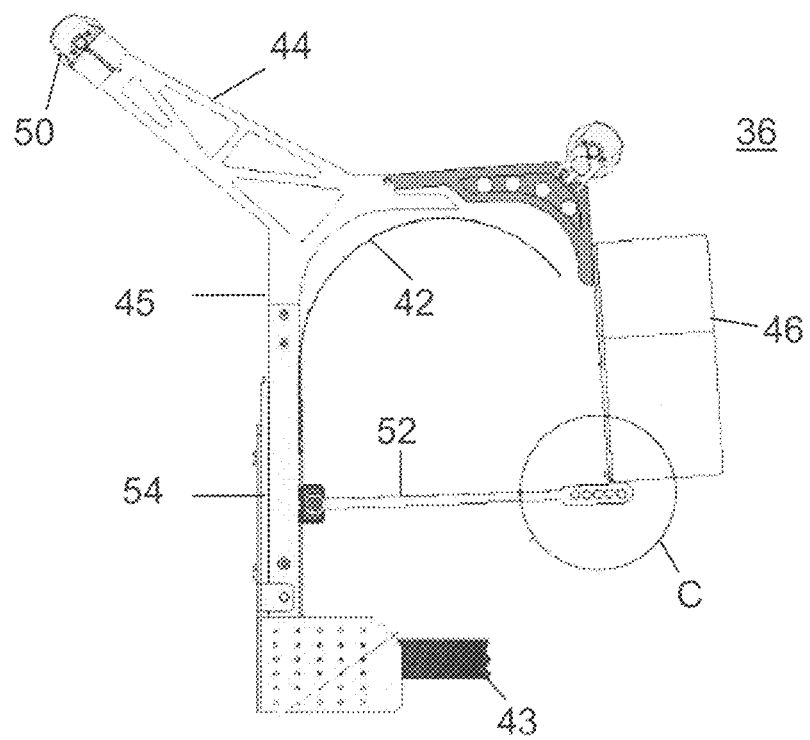
FIG. 36 is a left side view showing a side bar which connects the front frame and the rear frame of the body wearable unit of the first modification shown in FIG. 24 to each other along a side of a user while broadening the width between the front frame and the rear frame.
Figure 37:
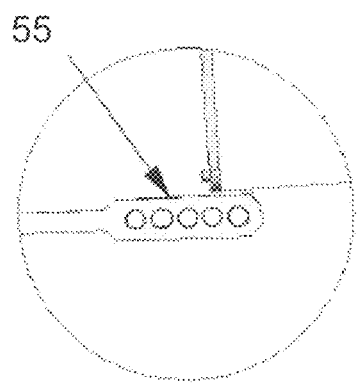
FIG. 37 is an enlarged view of a connection portion D of the side bar which connects the front frame and the rear frame shown in FIG. 36.

FIG. 34 is a left side view showing a side bar 52 which connects the front frame 45 and a rear frame 46 of the body wearable unit 36 of the first modification shown in FIG. 24 to each other along a side of a user while narrowing a width between the front frame 45 and the rear frame 46. FIG. 35 is an enlarged view of a connection portion C of the side bar 52 which connects the front frame 45 and the rear frame 46 shown in FIG. 34. FIG. 36 is a left side view showing the side bar 52 which connects the front frame 45 and the rear frame 46 of the body wearable unit 36 of the first modification shown in FIG. 24 to each other along a side of a user while broadening the width between the front frame 45 and the rear frame 46. FIG. 37 is an enlarged view of a connection portion D of the side bar 52 which connects the front frame 45 and the rear frame 46 shown in FIG. 36.

The body wearable unit 36 of the first modification includes a width adjustment mechanism between the front frame 45 and the rear frame 46. Specifically, the width adjustment mechanism between the front frame 45 and the rear frame 46 is constituted of the side bar 52 which connects the front frame 45 and the rear frame 46 to each other along a side of a user such that the width between the front frame 45 and the rear frame 46 is variable. A width adjustment unit 55 which adjusts a frame width between the front frame 45 and the rear frame 46 is provided to a distal end of the side bar 52. By changing a connection portion of the side bar 52 with the rear frame 46 by the width adjustment unit 55 provided to the distal end of the side bar 52, the width between the front frame 45 and the rear frame 46 can be narrowed (FIG. 34, FIG. 35) or the width between the front frame 45 and the rear frame 46 can be broadened (FIG. 36, FIG. 37).

The width adjustment mechanism between the front frame 45 and the rear frame 46 is not limited to the width adjustment unit 55 of the side bar 52.

(Second Modification: Body Wearable Unit 38: Front Holding Type Wearable Unit)

Figure 38:
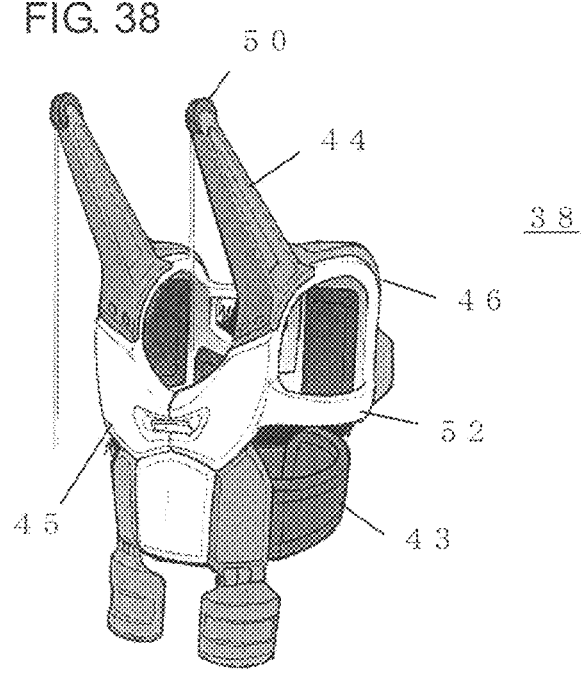
FIG. 38 is a schematic perspective view showing the constitution of a body wearable unit of a second modification used in the support device according to the first embodiment.
Figure 39:
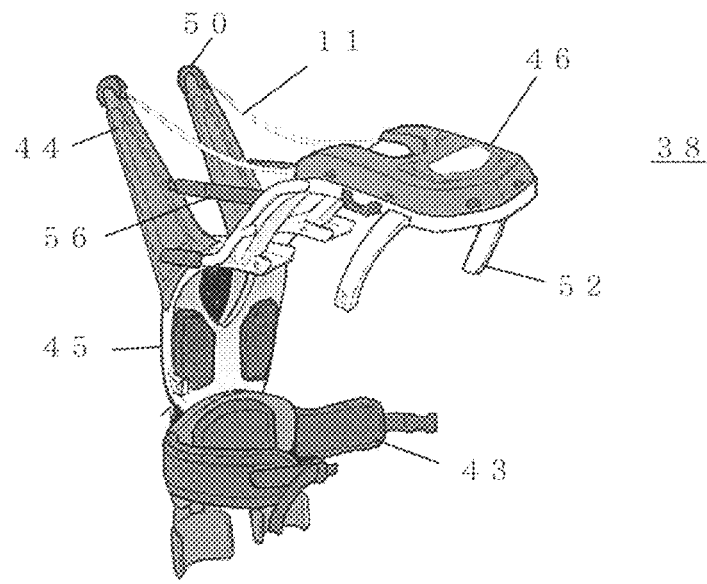
FIG. 39 is a perspective view showing a state where the rear frame of the body wearable unit shown in FIG. 38 is opened upward.
Figure 40:
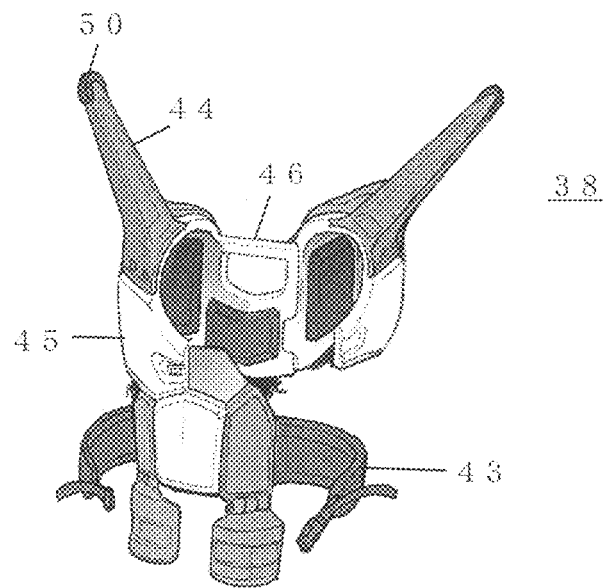
FIG. 40 is a perspective view showing a state where a portion of the rear frame of the body wearable unit shown in FIG. 38 is opened sideward.
Figure 41:
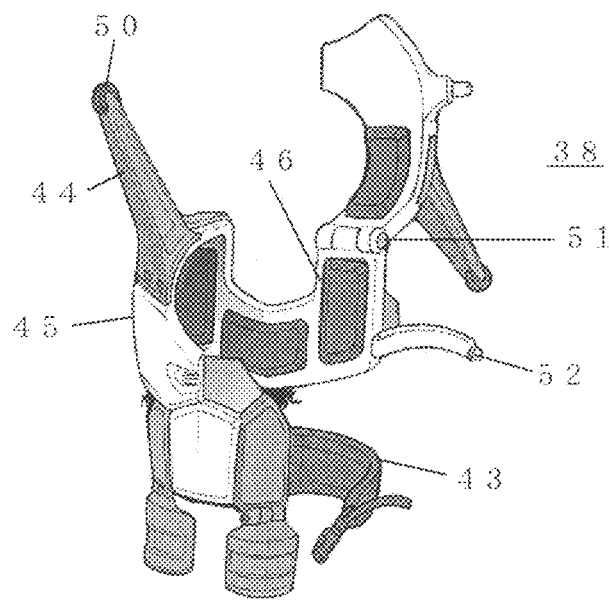
FIG. 41 is a perspective view showing a state where a portion of the front frame and an arm of the body wearable unit shown in FIG. 38 are opened upward.

FIG. 38 is a schematic perspective view showing the constitution of a body wearable unit 38 of a second modification used in the support device according to the first embodiment. FIG. 39 is a perspective view showing a state where a rear frame 46 of the body wearable unit 38 shown in FIG. 38 is opened upward. FIG. 40 is a perspective view showing a state where a portion of the rear frame 46 of the body wearable unit 38 shown in FIG. 38 is opened sideward. FIG. 41 is a perspective view showing a state where a portion of a front frame 45 and an arm 44 of the body wearable unit shown in FIG. 38 are opened upward.

By comparison, the body wearable unit 38 of the second modification differs from the body wearable unit 36 of the first modification shown in FIG. 24 with respect to a point where while the body wearable unit 36 of the first modification is formed of a member made of metal and having a straight-line shape, the body wearable unit 38 of the second modification is formed of a member made of resin and having a curved shape. The body wearable unit 38 of the second modification may be formed using a resin-made member having predetermined rigidity. The body wearable unit 38 of the second modification differs from the body wearable unit 36 of the first modification with respect to a point where the body wearable unit 38 of the second modification does not have the slide frame 54. However, the body wearable unit 38 of the second modification may also have the slide frame 54.

The body wearable unit 38 of the second modification also has a frame open/close mechanism in the same manner as the body wearable unit 36 of the first modification.

In the frame open/close mechanism shown in FIG. 39, in the same manner as the body wearable unit 36 of the first modification, a rear frame 46 can be upwardly opened or closed. Further, in the body wearable unit 38 of the second modification, the rear frame 46 and an arm 44 are connected to each other, and the body wearable unit 38 includes a damper 56 which applies a buffering action to the respective movements of the rear frame 46 and an arm 44. Due to such a constitution, when the rear frame 46 is opened or closed, an open/close operation of the rear frame 46 is buffered by the damper 56 so that the gentle open/close operation can be realized. Accordingly, it is possible to suppress the falling of the body wearable unit 38 at the time of opening or closing the rear frame 46 and hence, the support device can be used more safely.

In the frame open/close mechanism shown in FIG. 40, a bent portion which is bendable along the vertical direction on a left side of the rear frame 46 is provided, and at least a side of the rear frame 46 is openable or closable sideward.

Due to such a constitution, a user can enter the body wearable unit 38 of the second modification from a side and hence, a user can easily wear the body wearable unit 38.

In the frame open/close mechanism shown in FIG. 41, in the same manner as the body wearable unit 36 of the first modification shown in FIG. 29, the front frame 45 and the rear frame are connected to each other by the hinge portion 51. On the other hand, different from the case shown in FIG. 29, in the case shown in FIG. 41, a part of the front frame 45 and the arm 44 are separated from the front frame 45 and are openable and closable upward.

Also in this case, a user can enter the body wearable unit 38 of the second modification from a side and hence, a user can easily wear the body wearable unit 38.

In the body wearable unit 38 of the second modification described above, as shown in FIG. 39 to FIG. 41, various frame open/close mechanisms can be realized.

(Advantages of Front Holding Type Wearable Unit)

Figure 42A:
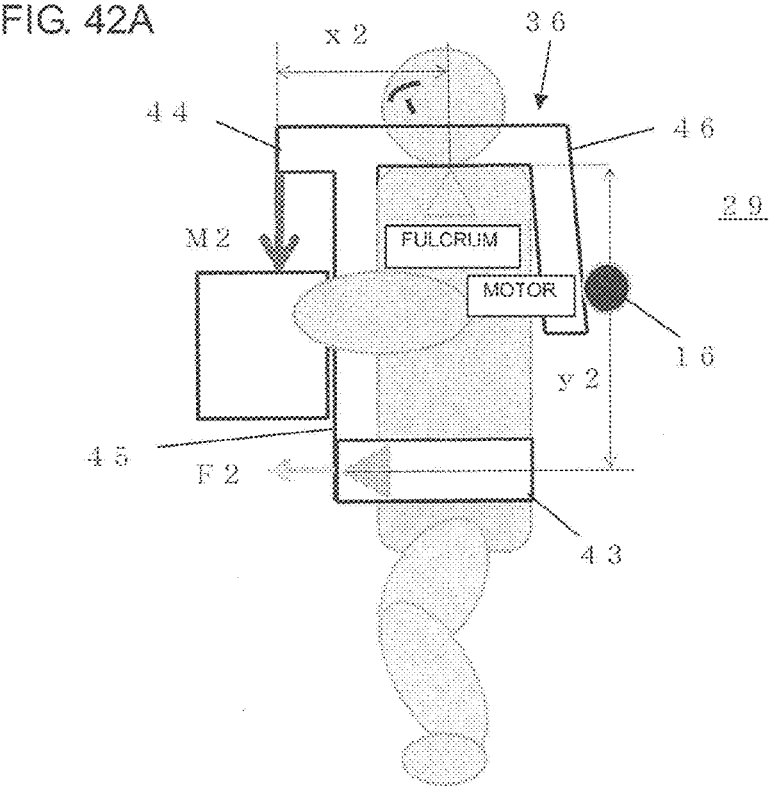
FIG. 42A is a side view of a support device which uses the body wearable unit of the first modification shown in FIG. 24, and shows a position of a fulcrum of the support device and a moment applied to a body.
Figure 42B:
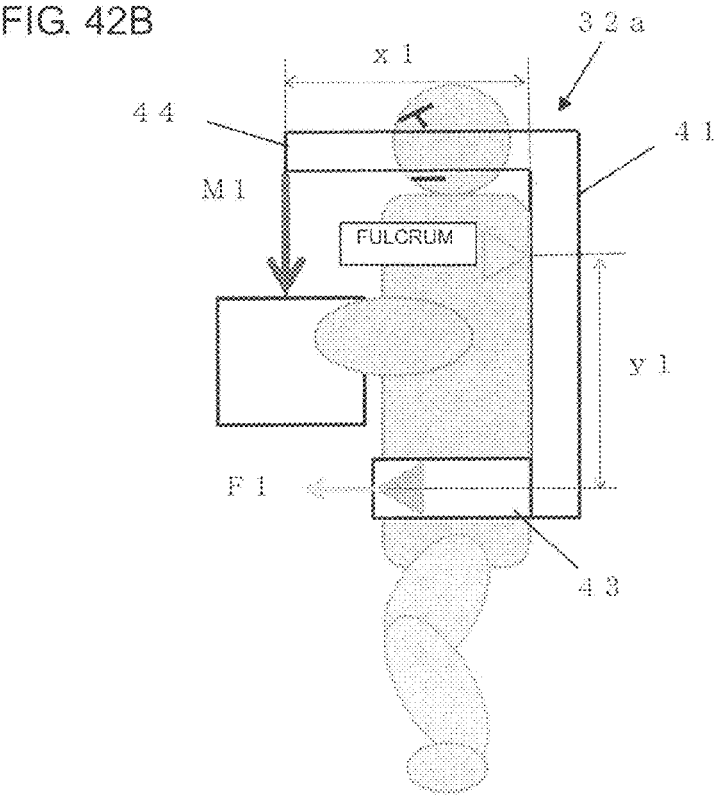
FIG. 42B is a side view of a support device which uses the body wearable unit of the first modification shown in FIG. 24, and shows a position of a fulcrum of the support device shown in FIG. 9 and a moment applied to a body.

Further, out of advantages acquired by the support device 29 which uses the body wearable units 36, 38 each in the form of a front holding type wearable unit, in particular, advantages acquired by arranging a load and a heavy object in a well-balanced manner using shoulders as fulcrums are explained with reference to FIG. 42A and FIG. 42B. FIG. 42A is a side view of a support device which uses the body wearable units 36, 38 (front holding type wearable units) of the modification shown in FIG. 24 showing a position of a fulcrum of the support device and a moment applied to a body of a user, and FIG. 42B is a side view of the support device which uses a body wearable unit 32a in the form of a bag pack type wearable unit shown in FIG. 9 showing a position of a fulcrum of the support device 29 and a moment applied to a body of a user.

According to the body wearable units 36, 38 each in the form of a front holding type wearable unit, as shown in FIG. 42A, it is possible to place fulcrums for supporting the support device 29 on shoulders of a user by arranging a load and a heavy object in a well-balanced manner. On the other hand, in the support device using the body wearable unit 32a in the form of the back pack type wearable unit, as shown in FIG. 42B, the fulcrums are placed on a rear side where the back rest portion 41 is disposed. Assuming that a weight of load is equal, the magnitude of a moment M2 shown in FIG. 42A and the magnitude of a moment M1 shown in FIG. 42B differ (M2<M1) depending on a distance from the fulcrum. As a result, with respect to a force which is applied to an abdominal part by the waist belt 43, a force F2 in FIG. 42A becomes smaller than a force F1 in FIG. 42B (F2<F1).

Specifically, the moments M2, M1 are expressed as products of the magnitudes of the loads and distances x2, x1 from fulcrum to the load, and the moments M2, M1 are balanced with products of the forces F2, F1 applied to the body and distances y2, y1 from the fulcrum to the abdominal part.

$$M2=(\text{load}) \times x2 = F2 \times y2 \qquad (1)$$

$$M1=(\text{load}) \times x1 = F1 \times y1 \qquad (2)$$

In FIG. 42A, the fulcrums are on the shoulders and hence, compared to the case shown in FIG. 42B, the relationship of x2<x1 and the relationship of y2>y1 are established.

Accordingly, when the magnitudes of the loads are equal in the above-mentioned formulae (1) and (2), the moment M2 becomes smaller than the moment M1. As a result, the forces F2, F1 applied to the abdominal part have the relationship of F2<F1. That is, according to the support device 29 using the body wearable unit 36 in the form of the front holding type wearable unit shown in FIG. 24, by placing the fulcrums on the shoulders of a user, the force F2 which is applied to the abdominal part can be reduced. By arranging a heavy object such as a motor which constitutes the drive unit 16 on a rear side, the heavy object becomes a counterweight for the load and hence, the moments can be further reduced so that the force F2 applied to the abdominal part can be reduced.

<Operation Support Device>

When the support device 29 (operation support device 30a and the muscle strength training support device 30b) is configured to function as the operation support device 30a, the drive unit 16 is controlled such that a measured force applied to the intermediate element 2 is reduced depending on the movement of an upper limb or a lower limb of a user, thus supporting the movement of the upper limb or the lower limb of the user.

Specifically, when a user grips the gripping unit 12 and performs an operation of lifting the intermediate element 2 upward, as shown in FIG. 4A, the intermediate element 2 is moved upward. In this case, the first elastic member 3a is compressed and the second elastic member 3b is extended so that a downward force is applied to the intermediate element 2 from the first and second elastic members 3a, 3b. Then, when the linear potentiometer 4 detects that the position of the intermediate element 2 is directed upward, the motor (drive unit) 16 is driven so that the wire 11 is wound and is pulled upward, thus supporting an upward lifting operation by the user.

When the user grips the gripping unit 12 and performs an operation of pushing the intermediate element 2 downward, as shown in FIG. 4C, the intermediate element 2 moves downward. In this case, the first elastic member 3a is extended and the second elastic member 3b is compressed, so that an upward force is applied to the intermediate element 2 from the first and second elastic members 3a, 3b. Then, when the linear potentiometer 4 detects that the position of the intermediate element 2 is directed downward, the motor (drive unit) 16 is driven so that the wire 11 is wound reversely and is slackened, thus supporting a downward pushdown operation by the user.

<Operation Support Flowchart>

Figure 11:
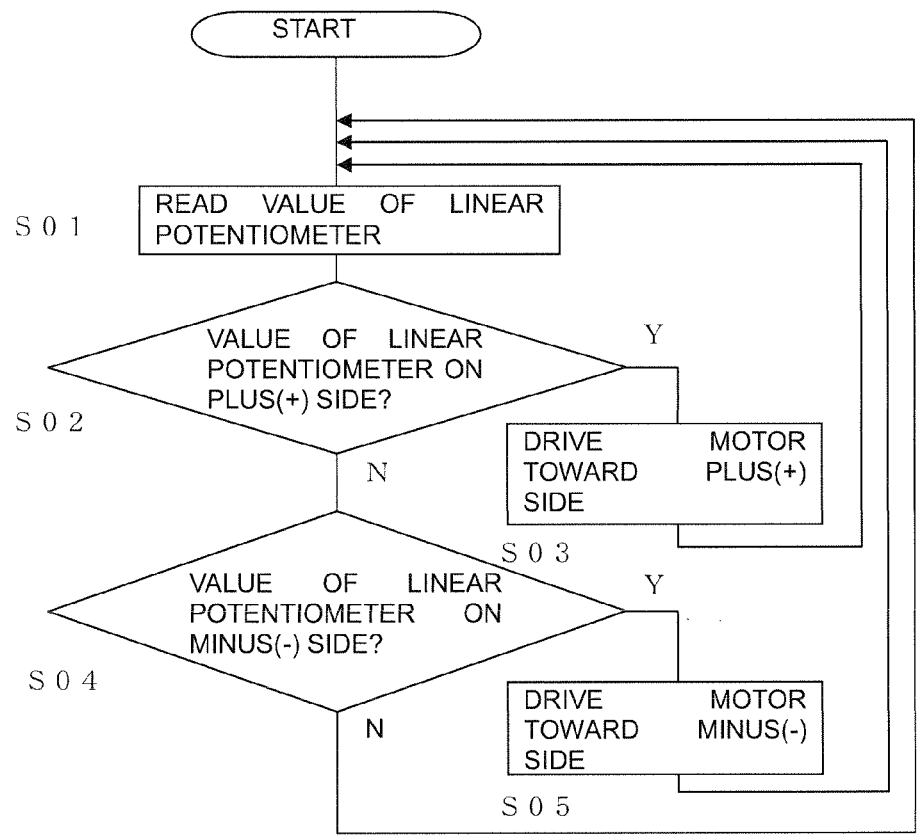
FIG. 11 is a flowchart explaining the manner of operation of the operation support device according to the first embodiment of this disclosure.

FIG. 11 is a flowchart explaining the manner of operation of the operation support device 30a according to the first embodiment of this disclosure.
(1) A value of the linear potentiometer 4 is read (S01).
(2) It is determined whether or not the value of the linear potentiometer 4 is in the upward (+) direction (S02). When the value of the linear potentiometer 4 is in the upward (+) direction, the motor 16 is driven so as to wind the wire 11, thus supporting an upward operation by the user (S03). Thereafter, the processing returns to the step S01, and the value of the linear potentiometer 4 is read again. On the other hand, when the value of the linear potentiometer 4 is not in the upward (+) direction, the processing advances to next step S04.
(3). It is determined whether or not the value of the linear potentiometer 4 is in the downward (−) direction (S04). When the value of the linear potentiometer 4 is in the downward (−) direction, the motor 16 is driven so as to release the wire 11, thus supporting a downward operation by the user (S05). Thereafter, the processing returns to the step S01, and the value of the linear potentiometer 4 is read again.

The above-mentioned steps are repeated hereinafter. Accordingly, the operation support device 30a ca support the movement of an upper limb or a lower limb of a user.

<Muscle Strength Training Support Device>

When the support device 29 (operation support device 30a and the muscle strength training support device 30b) is configured to function as the muscle strength training support device 30b, the drive unit 16 is controlled such that a measured force applied to the intermediate element 2 is increased depending on the movement of an upper limb or a lower limb of a user, thus supporting the muscle strength training of the upper limb or the lower limb of the user.

Specifically, when the linear potentiometer 4 detects that the position of the intermediate element 2 is directed upward from a predetermined value, it is understood that a force larger than a predetermined value is applied to an upper limb or a lower limb of a user in a preset muscle strength training. Accordingly, the motor (drive unit) 16 is driven so as to wind and pulls up the wire 11 thus bringing a force applied to the upper limb or the lower limb of the user to the force of the predetermined value, thus supporting the muscle strength training of the user.

When the linear potentiometer 4 detects that the position of the intermediate element 2 is downward from a predetermined value, it is understood that a force smaller than a predetermined value is applied to an upper limb or a lower limb of a user in a preset muscle strength training. Accordingly, the motor (drive unit) 16 is driven so as to rotate the wire 11 in the reverse direction thus loosen the wire 11. As a result, a force applied to the upper limb or the lower limb of the user is brought into a force of a predetermined value, thus supporting the muscle strength training of the user.

<Muscle Strength Training Support Flowchart>

Figure 12:
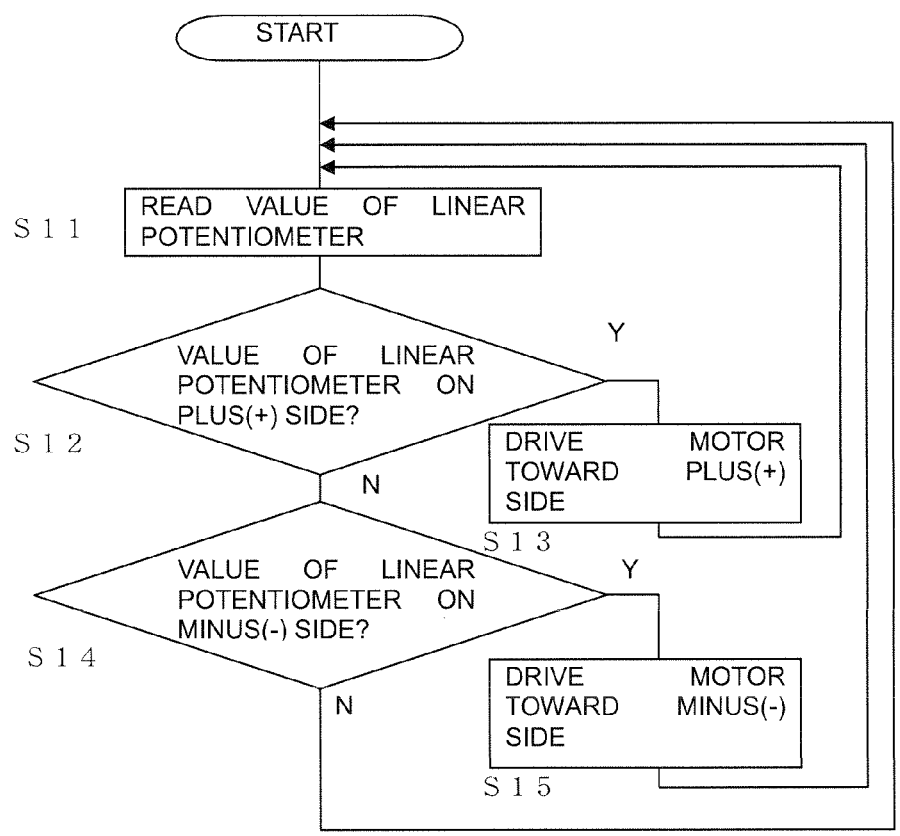
FIG. 12 is a flowchart explaining the manner of operation of a muscle strength training support device according to the first embodiment of this disclosure.

FIG. 12 is a flowchart explaining the manner of operation of a muscle strength training support device 30b according to the first embodiment of this disclosure.
(1) A value of the linear potentiometer 4 is read (S11).
(2) It is determined whether or not the value of the linear potentiometer 4 is in the upward (+) direction from a predetermined value (S12). When the value of the linear potentiometer 4 is in the upward (+) direction from the predetermined value, the motor 16 is driven so as to wind the wire 11, thus bringing a load to the predetermined value (S13). Thereafter, the processing returns to the step S11, and the value of the linear potentiometer 4 is read again. On the other hand, when the value of the linear potentiometer 4 is not in the upward direction from the predetermined value, the processing advances to next step S14.
(3) It is determined whether or not the value of the linear potentiometer 4 is in the downward (−) direction from the predetermined value (S14). When the value of the linear potentiometer 4 is in the downward (−) direction from the predetermined value, the motor 16 is driven so as to release the wire 11 thus bringing a load to the predetermined value (S15). Thereafter, the processing returns to the step S11, and the value of the linear potentiometer 4 is read again.

The above-mentioned steps are repeated hereinafter. Accordingly, the muscle strength training support device 30b ca support the muscle strength training of an upper limb or a lower limb of a user.

As can be clearly understood from the above-mentioned description, the support device 29 (operation support device 30a and the muscle strength training support device 30b) according to the first embodiment of this disclosure is configured such that the intermediate element 2 is supported by the first and second elastic members 3a, 3b and hence, even when a user performs a sudden movement, there is no possibility that the force measurement sensor structures 10, 10a will excessively react sensitively with the movement. Accordingly, it is possible to optimize the support device 29 (operation support device 30a and the muscle strength training support device 30b) within a range suitable for an operation by the user.

Particularly, when the support device 29 is used as the operation support device 30a, by adjusting the first and second elastic members 3a, 3b depending on the content of an operation, it is possible to enhance the above-mentioned characteristics in the upward direction and in the downward direction and hence, a load applied to a user can be reduced.

In the same manner, when the support device 29 is used as the muscle strength training support device 30b, by adjusting the first and second elastic members 3a, 3b depending on a function of a user to be recovered, the above-mentioned loads in the upward direction and in the downward direction can be optimized. That is, the loads optimum for the respective directions can be set. Accordingly, the user can perform training with a load optimum for the upward direction and training with a load optimum for the downward direction simultaneously and hence, a training time can be shortened.

Second Embodiment

Force Measurement Sensor Structure

Figure 13:
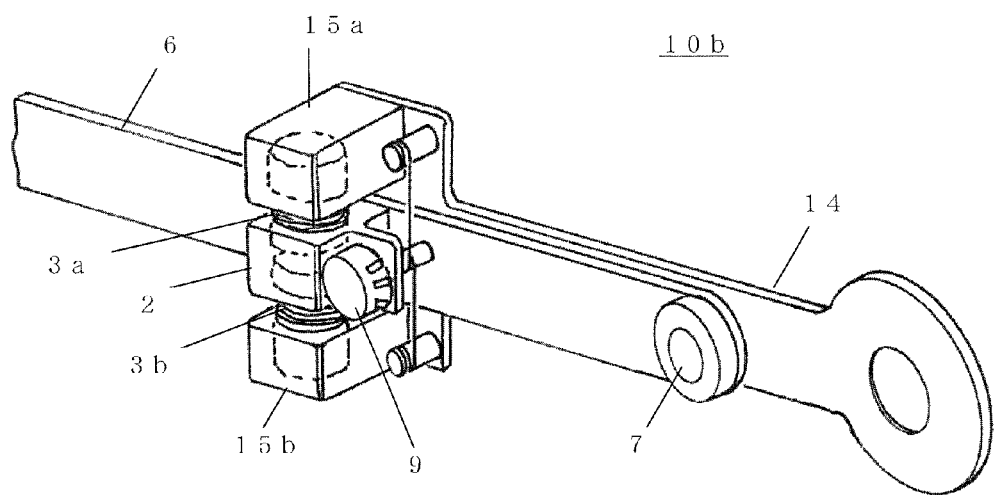
FIG. 13 is a perspective view showing the constitution of the force measurement sensor structure according to a second embodiment of this disclosure.
Figure 14:
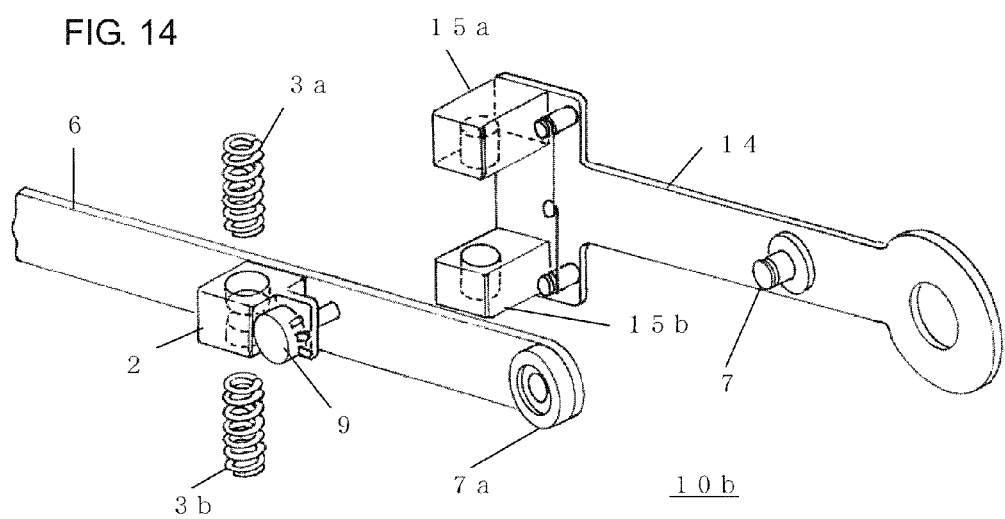
FIG. 14 is an exploded perspective view of the force measurement sensor structure shown in FIG. 13.

FIG. 13 is a perspective view showing the constitution of the force measurement sensor structure 10b according to a second embodiment of this disclosure. FIG. 14 is an exploded perspective view of the force measurement sensor structure 10b shown in FIG. 13.

The force measurement sensor structure 10b includes: a measurement element 6 which has enough length to rotate about a fulcrum 7; an intermediate element 2 provided on the measurement element 6 at a predetermined position; first and second elastic members 3a, 3b which are provided at both ends of the intermediate element 2 with respect to the direction which intersects with the extending direction of the measurement element 6 and supports the intermediate element 2; and a rotational potentiometer 9 which is connected to the intermediate element 2 and detects a change in a rotational angle of the intermediate element 2 in an arc which connects the first elastic member 3a and the second elastic member 3b. The first and second elastic members 3a, 3b are configured to apply a load to the intermediate element 2 in the directions opposite to each other in the rotational direction about a fulcrum 7 of the intermediate element 2 along the arc. Further, a force applied to the intermediate element 2 can be measured by detecting a change in a rotational angle of the intermediate element 2 in the above-mentioned arc using the rotational potentiometer 9.

A rotational shaft which constitutes the fulcrum 7 of the measurement element 6 is provided on a base 14. An upper end of the first elastic member 3a is received by a first spring receiver 15a, and a lower end of the second elastic member 3b is received by a second spring receiver 15b. The first and second spring receivers 15a, 15b are provided on the base 14. The fulcrum 7 provided on the base 14 is fitted into a bearing 7a provided on the measurement element 6.

Hereinafter, the members which constitute the force measurement sensor structure 10b are explained.

<Measurement Element>

The measurement element 6 is provided rotatable relative to the rotary shaft (fulcrum) 7. The intermediate element 2 is provided at a predetermined position of the measurement element 6. It is preferable that the measurement element 6 be made of a rigid material for measuring a force applied to the intermediate element 2. As a material for forming the measurement element 6, any material can be used provided that the material is a rigid material. For example, a material which is usually used in the force measurement such as iron, stainless steel, aluminum, wood or bamboo can be used.

<Intermediate Element>

The intermediate element 2 is provided at a predetermined position of the measurement element 6. As a material for the intermediate element 2, any material can be used provided that the material is usually used in the force measurement such as iron, stainless steel, aluminum, wood or bamboo, for example.

<First and Second Elastic Members>

The first elastic member 3a and the second elastic member 3b are provided at both ends of the intermediate element 2 in the direction which intersects with the direction that the measurement element 6 extends, and support the intermediate element 2. The first and second elastic members 3a, 3b are configured to apply a load to the intermediate element 2 in the directions opposite to each other of the rotational direction about the fulcrum 7 of the intermediate element 2 along the above-mentioned arc which connects the first elastic member 3a, the intermediate element 2 and the second elastic member 3b.

<Rotational Potentiometer>

The rotational potentiometer 9 is connected to the intermediate element 2, and detects a change in a rotational angle of the intermediate element 2 along an arc which connects the first elastic member 3a, the intermediate element 2 and the second elastic member 3b. A force applied to the intermediate element 2 can be detected by detecting a change in a rotational angle of the intermediate element 2 along the arc by the rotational potentiometer 9.

Figure 15A:
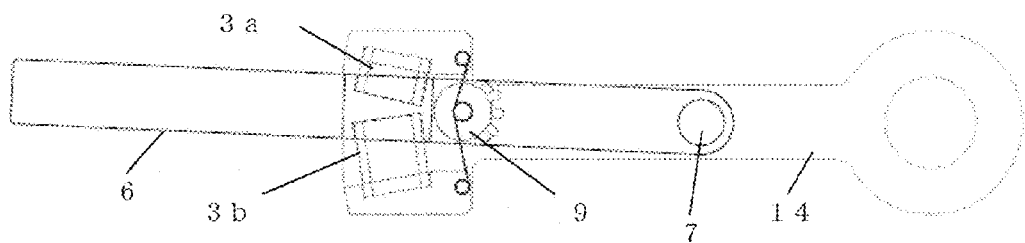
FIG. 15A is a front view of the force measurement sensor structure shown in FIG. 13, and shows a position of an intermediate element when a force in the clockwise (+) direction is applied to the intermediate element so that the intermediate element is moved in the clockwise (+) direction.
Figure 15B:
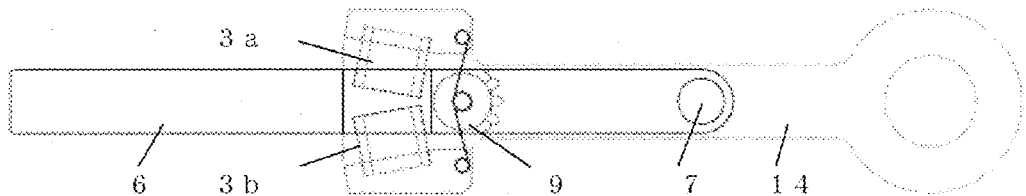
FIG. 15B is a front view of the force measurement sensor structure shown in FIG. 13, and shows the position of the intermediate element when a force is not applied to the intermediate element.
Figure 15C:
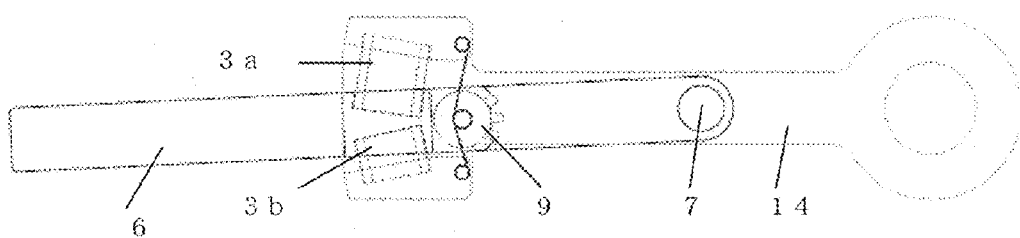
FIG. 15C is a front view of the force measurement sensor structure shown in FIG. 13, and shows the position of the intermediate element when a force is applied to the intermediate element in the counterclockwise (−) direction so that the intermediate element is moved in the counterclockwise (−) direction.

FIG. 15A is a front view of the force measurement sensor structure 10b shown in FIG. 13 showing a position of the intermediate element 2 when a force in the clockwise (+) direction is applied to the intermediate element 2 so that the intermediate element 2 is moved in the clockwise (+) direction. FIG. 15B is the front view of the force measurement sensor structure 10b shown in FIG. 13 showing the position of the intermediate element 2 when a force is not applied to the intermediate element 2. FIG. 15C is the front view of the force measurement sensor structure 10b shown in FIG. 13 showing the position of the intermediate element 2 when a force is applied to the intermediate element 2 in the counterclockwise (−) direction so that the intermediate element 2 is moved in the counterclockwise (−) direction.

As shown in FIG. 15A, when the intermediate element 2 is positioned in the clockwise (+) direction, the first elastic member 3a is compressed and the second elastic member 3b is extended and hence, a load in the counterclockwise (−) direction is applied to the intermediate element 2 from the first and second elastic members 3a, 3b. On the other hand, as shown in FIG. 15C, when the intermediate element 2 is positioned in the counterclockwise (−) direction, the first elastic member 3a is extended and the second elastic member 3b is compressed and hence, a load in the clockwise (+) direction is applied to the intermediate element 2 from the first and second elastic members 3a, 3b. In the force measurement sensor structure 10b, a load applied to the intermediate element 2 is measured by measuring a change in a rotational angle of the intermediate element 2 along an arc which connects the first elastic member 3a, the intermediate element 2 and the second elastic member 3b using the rotational potentiometer 9. For example, it is understood that when the position of the intermediate element 2 is in the clockwise (+) direction, a load in the counterclockwise (−) direction is applied to the intermediate element 2. On the other hand, it is understood that when the position of the intermediate element 2 is in the counterclockwise (−) direction, a load in the in the clockwise (+) direction is applied to the intermediate element 2.

<Load Control Device>

Figure 16:
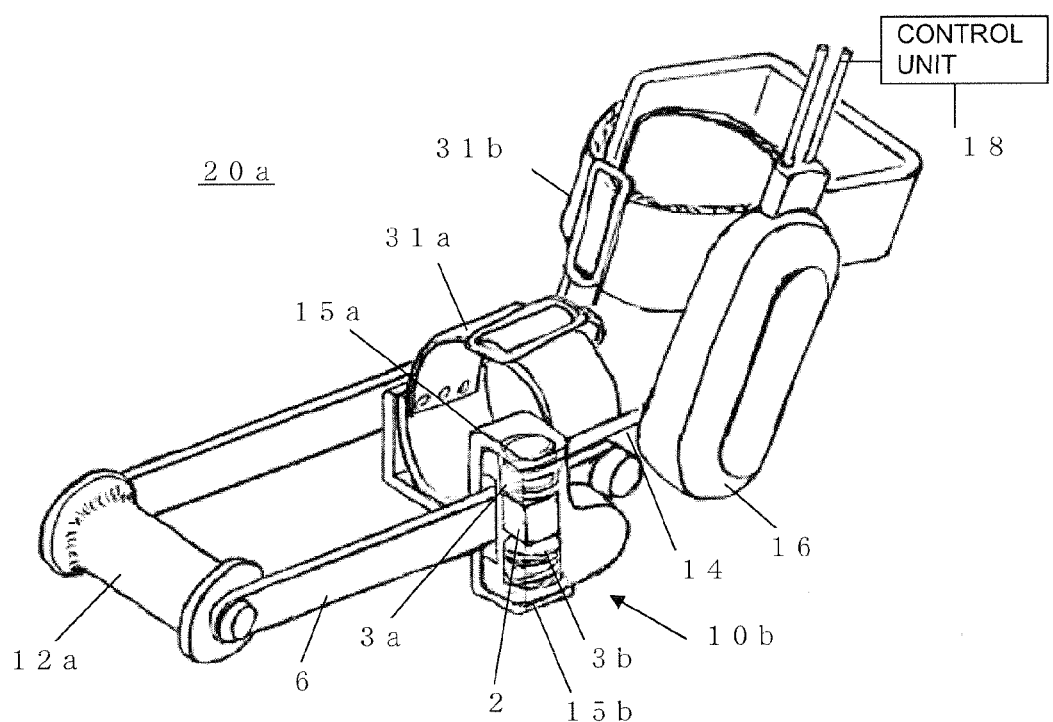
FIG. 16 is a perspective view showing the constitution of a load control device according to the second embodiment of this disclosure.
Figure 17:
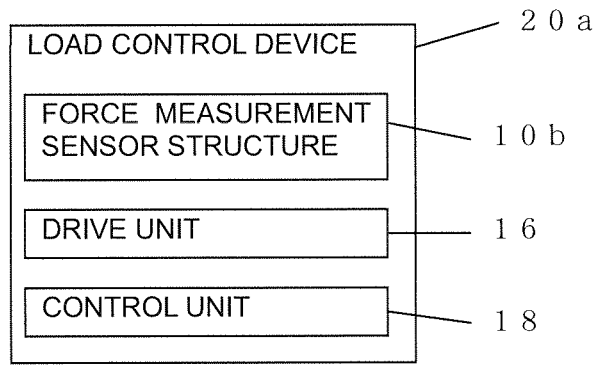
FIG. 17 is a block diagram showing the functional constitution of the load control device shown in FIG. 16.

FIG. 16 is a perspective view showing the constitution of a load control device 20a according to the second embodiment of this disclosure. FIG. 17 is a block diagram showing the functional constitution of the load control device 20a shown in FIG. 16.

As shown in FIG. 16 and FIG. 17, the load control device 20a includes: the force measurement sensor structure 10b; a motor (drive unit) 16 which rotates a base 14 on which first and second spring receivers 15a, 15b are provided; and a control unit 18 which controls the motor (drive unit) 16. A gripping unit 12a which a user can grip with either hand is provided on a distal end of a measurement element 6. The user can wear the load control device 20a on his upper arm by means of upper arm wearable units 31a, 31b. By rotating the base 14 on which the first and second spring receivers 15a, 15b are provided by the above-mentioned motor (drive unit) 16, it is possible to vary a load applied to the intermediate element 2 from the first and second elastic members 3a, 3b.

Hereinafter, the members which constitute the load control device 20a are explained.

<Drive Unit>

The drive unit 16 can be provided by, for example, a motor or the like which can rotate the base 14 on which the first and second spring receivers 15a, 15b are provided. The constitution of the drive unit 16 is not limited to a motor, and any means can be used provided that the means can vary a load applied to the intermediate element 2 from the first and second elastic members 3a, 3b. For example, a load applied to the intermediate element 2 from the first elastic member 3a and the second elastic member 3b may be varied by changing the relative position of the intermediate element 2 upward or downward with respect to the first elastic member 3a and the second elastic member 3b.

<Control Unit>

Figure 18:
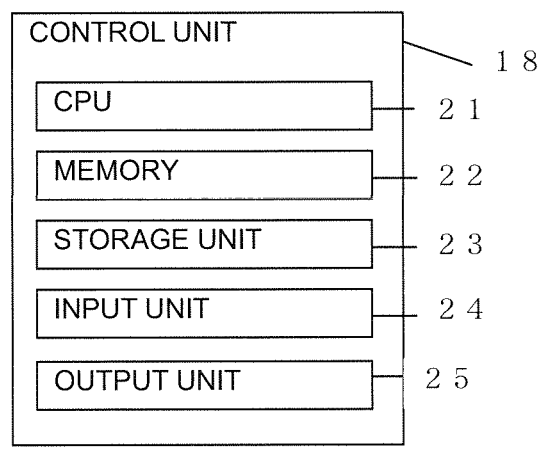
FIG. 18 is a block diagram showing a physical constitutional example of a control unit shown in FIG. 17.
Figure 19:
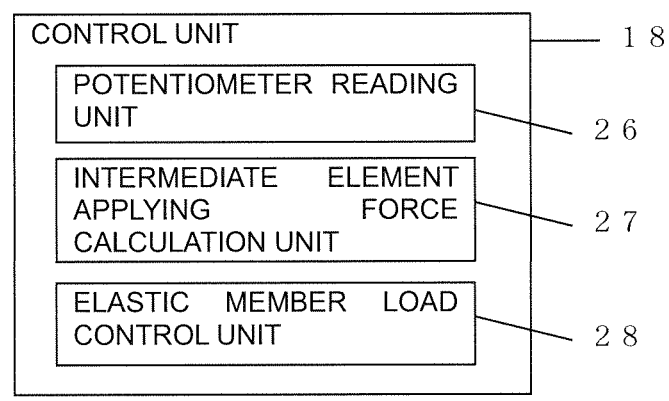
FIG. 19 is a block diagram showing the functional constitutional example of the control unit shown in FIG. 17.

FIG. 18 is a block diagram showing a physical constitutional example of the control unit 18 shown in FIG. 17. FIG. 19 is a block diagram showing a functional constitutional example of the control unit 18 shown in FIG. 17.

The control unit 18 may be, for example, as shown in FIG. 18, realized by a personal computer which includes: a CPU 21; a memory 22; a storage unit 23; an input unit 24; an output unit 25 and the like. The functional constitution of the control unit 18 may include: as shown in FIG. 19, a potentiometer reading unit 26 which reads a value of a potentiometer; an intermediate element applied force calculation unit 27 which calculates a force applied to the intermediate element 2; and an elastic member load control unit 28 which controls a load applied to the intermediate element 2 from the first and second elastic members 3a, 3b.

<Operation Support Device and Muscle Strength Training Support Device>

Figure 20:
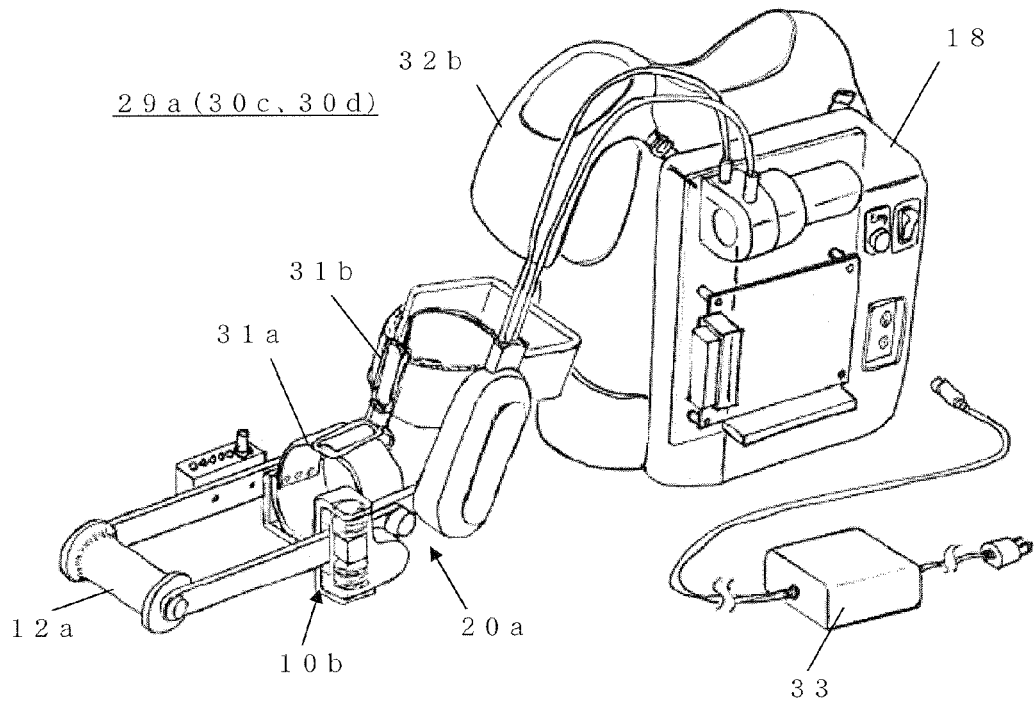
FIG. 20 is a perspective view showing the constitution of an operation support device/a muscle strength training support device according to the second embodiment of this disclosure.
Figure 21:
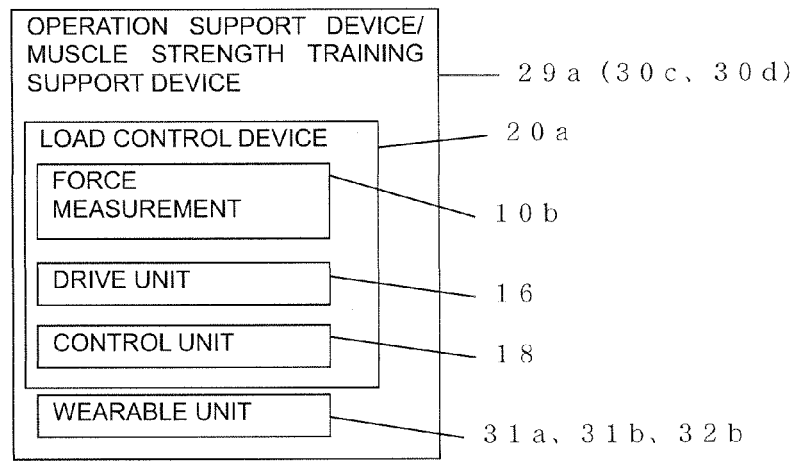
FIG. 21 is a block diagram showing the functional constitution of the operation support device/muscle strength training support device shown in FIG. 20.

FIG. 20 is a perspective view showing the constitution of a support device 29a (an operation support device 30c/a muscle strength training support device 30d) according to the second embodiment of this disclosure. FIG. 21 is a block diagram showing a functional constitution of the support device 29a (operation support device 30c/muscle strength training support device 30d) shown in FIG. 20.

The support device 29a (the operation support device 30c and the muscle strength training support device 30d) includes the above-mentioned load control device 20a, the upper arm wearable units 31a, 31b, and a body wearable unit 32b. The force measurement sensor structure 10a of the load control device 20a includes the gripping unit 12a. The gripping unit 12a is, as shown in FIG. 16, connected to the intermediate element 2 of the force measurement sensor structure 10b. A force is transmitted to the intermediate element 2 in an interlocking manner with the movement of an upper limb or a lower limb of a user. Specifically, the gripping unit 12a is provided for enabling the user to grip the gripping unit 12 with either hand, thus easily applying a force to the force measurement sensor structure 10b. Although the gripping unit 12a is formed into a shape so that a user can grip the gripping unit 12a with either hand in the example shown in FIG. 20, the gripping unit 12a is not limited to the example shown in FIG. 20, and the gripping unit 12a may be fixed to an upper limb or a lower limb of a user such that the gripping unit 12b can be moved in an interlocking manner with the upper limb or the lower limb of a user. Further, the user may easily wear the force measurement sensor structure 10b using the upper arm wearable units 31a, 31b. The control unit 18, a power source 33 and the like may be provided on the body of a user using the body wearable unit 32b. The upper arm wearable units 31a, 31b and the body wearable unit 32b are not indispensable for the constitution of the support device 29a (operation support device 30c and the muscle strength training support device 30d).

<Operation Support Device>

When the support device 29a (operation support device 30c and the muscle strength training support device 30d) is configured to function as the operation support device 30c, the drive unit 16 is controlled such that a measured force applied to the intermediate element 2 is reduced depending on the movement of an upper limb or a lower limb of a user, thus supporting the movement of the upper limb or the lower limb of the user.

Specifically, when a user grips the gripping unit 12a and performs an operation of lifting the intermediate element 2 in the clockwise (+) direction, as shown in FIG. 15A, the intermediate element 2 is moved in the clockwise (+) direction. In this case, the first elastic member 3a is compressed and the second elastic member 3b is extended so that a force in the counterclockwise (−) direction is applied to the intermediate element 2 from the first and second elastic members 3a, 3b. Then, when the rotational potentiometer 9 detects that a rotational angle of the intermediate element 2 is in the clockwise (+) direction, the motor (drive unit) 16 is driven so that the base 14 is rotated in the clockwise (+) direction, thus supporting a lifting operation in the clockwise (+) direction by the user.

When the user grips the gripping unit 12a and performs the operation of pushing down the intermediate element 2 in the counterclockwise (−) direction, as shown in FIG. 15C, the intermediate element 2 is moved in the counterclockwise (−) direction. In this case, the first elastic member 3a is extended and the second elastic member 3b is compressed so that a force in the clockwise (+) direction is applied to the intermediate element 2 from the first and second elastic members 3a, 3b. Then, when the rotational potentiometer 9 detects that a rotational angle of the intermediate element 2 is in the counterclockwise (−) direction, the motor (drive unit) 16 is driven so that the base 14 is rotated in the counterclockwise (−) direction, thus supporting a downward pushdown operation in the counterclockwise (−) direction by the user.

<Operation Support Flowchart>

Figure 22:
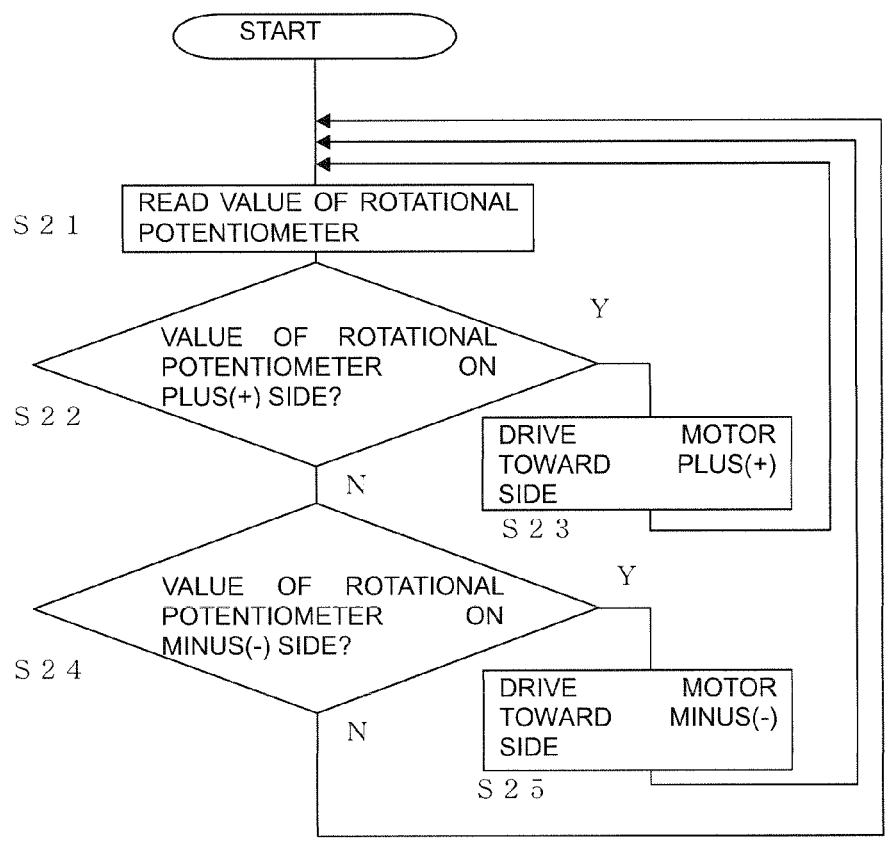
FIG. 22 is a flowchart explaining the manner of operation of the operation support device according to the second embodiment of this disclosure.

FIG. 22 is a flowchart explaining the manner of operation of the operation support device 30c according to the second embodiment of this disclosure.

(1) A value of the rotational potentiometer 9 is read (S21).
(2) It is determined whether or not the value of the rotational potentiometer 9 is in the clockwise (+) direction (S22). When the value of the rotational potentiometer 9 is in the clockwise (+) direction, the motor 16 is driven so as to support an operation in the clockwise (+) direction, thus rotating the base 14 in the clockwise (+) direction (S23). Thereafter, the processing returns to the step S21, and the value of the rotational potentiometer 9 is read again. On the other hand, when the value of the rotational potentiometer 9 is not in the clockwise (+) direction, the processing advances to next step S24.
(3). It is determined whether or not the value of the rotational potentiometer 9 is in the counterclockwise (−) direction (S24). When the value of the rotational potentiometer 9 is in the counterclockwise (−) direction, the motor 16 is driven so as to support an operation in the counterclockwise (−) direction by the user, thus rotating the base 14 in the counterclockwise (−) direction (S25). Thereafter, the processing returns to the step S21, and the value of the rotational potentiometer 9 is read again.

The above-mentioned respective steps are repeated hereinafter. Accordingly, the operation support device 30c ca support the movement of an upper limb or a lower limb of a user.

<Muscle Strength Training Support Device>

When the support device 29a (operation support device 30c and the muscle strength training support device 30d) is configured to function as the muscle strength training support device 30d, the drive unit 16 is controlled such that a measured force applied to the intermediate element 2 is increased depending on the movement of an upper limb or a lower limb of a user, thus supporting the muscle strength training of the upper limb or the lower limb of the user.

Specifically, when the rotational potentiometer 9 detects that the position of the intermediate element 2 is in the clockwise (+) direction from a predetermined value, it is understood that a force larger than a force of a predetermined value which is set in advance and is applied to an upper limb or a lower limb of a user in muscle strength training is applied to the upper limb or the lower limb of the user. Accordingly, the motor (drive unit) 16 is driven so as to rotate the base 14 in the clockwise (+) direction thus bringing a force applied to the upper limb or the lower limb of the user to the force of the predetermined value, thus supporting the muscle strength training of the user.

When the rotational potentiometer 9 detects that the position of the intermediate element 2 is in the counterclockwise (−) direction from a predetermined value, it is understood that a force smaller than a force of a predetermined value which is set in advance and is applied to an upper limb or a lower limb of a user in muscle strength training is applied to the upper limb or the lower limb of the user. Accordingly, the motor (drive unit) 16 is driven so as to rotate the base 14 in the counterclockwise (−) direction, thus bringing a force applied to the upper limb or the lower limb of the user to the force of the predetermined value, thus supporting the muscle strength training of the user.

In the muscle strength training support device 30d, the rotational potentiometer 9 detects a rotational angle of the intermediate element 2, and sets a load applied to a user to a fixed load by decreasing a force applied to a user when the force larger than a predetermined force and by increasing a force applied to a user when the force is smaller than a predetermined force. Accordingly, in the muscle strength training of a user, the muscle strength training support device 30d can maintain a fixed load irrelevant to the motion of the user.

<Muscle Strength Training Support Flowchart>

Figure 23:
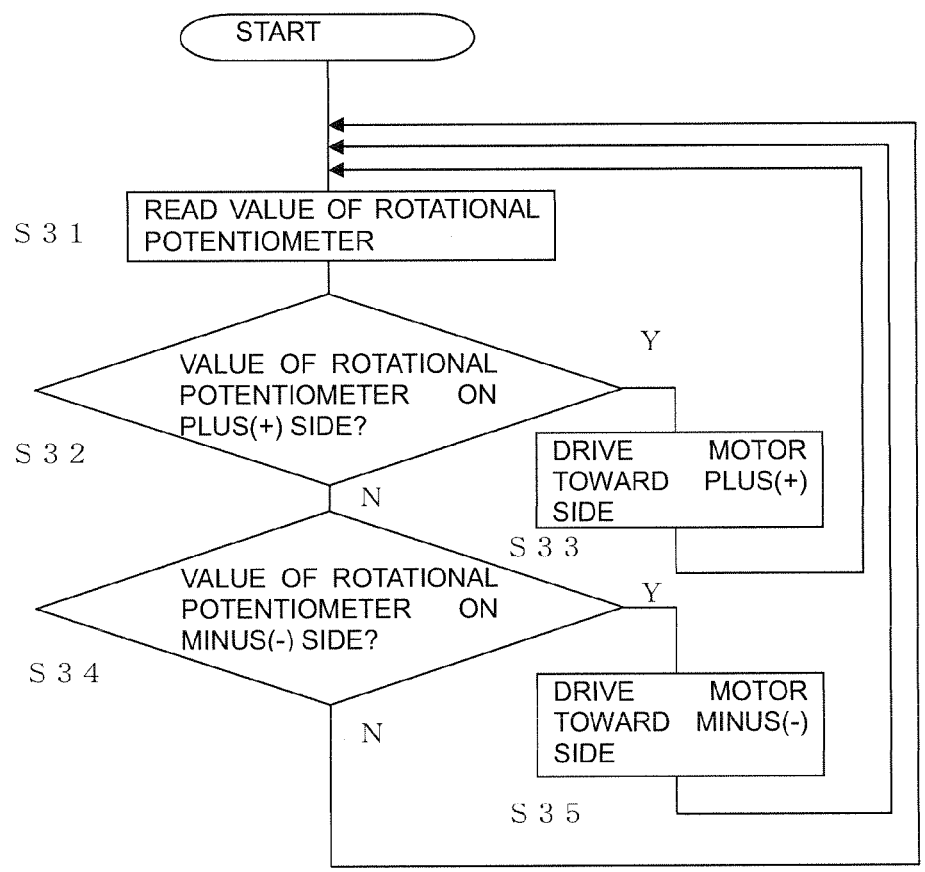
FIG. 23 is a flowchart explaining the manner of operation of a muscle strength training support device according to the second embodiment of this disclosure.

FIG. 23 is a flowchart explaining the manner of operation of a muscle strength training support device 30d according to the second embodiment of this disclosure.

(1) A value of the rotational potentiometer 9 is read (S31).

(2) It is determined whether or not the value of the rotational potentiometer 9 is in the clockwise (+) direction from a predetermined value (S32). When the value of the rotational potentiometer 9 is in the clockwise (+) direction from the predetermined value, the motor is driven so as to rotate the base in the clockwise (+) direction, thus bringing a load to the predetermined value (S33). Thereafter, the processing returns to the step S31, and the value of the rotational potentiometer 9 is read again. On the other hand, when the value of the rotational potentiometer 9 is not in the clockwise direction from the predetermined value, the processing advances to next step S34.

(3) It is determined whether or not the value of the rotational potentiometer 9 is in the counterclockwise (−) direction from the predetermined value (S34). When the value of the rotational potentiometer 9 is in the counterclockwise (−) direction from the predetermined value, the motor is driven so as to rotate the base in the counterclockwise (−) direction, thus bringing a load to the predetermined value (S35). Thereafter, the processing returns to the step S31, and the value of the rotational potentiometer 9 is read again.

The above-mentioned respective steps are repeated hereinafter. Accordingly, the muscle strength training support device 30d ca support the muscle strength training of an upper limb or a lower limb of a user.

As can be clearly understood from the above-mentioned description, the support device 29a (operation support device 30c and the muscle strength training support device 30d) according to the second embodiment of this disclosure is configured such that the intermediate element 2 is supported by the first and second elastic members 3a, 3b and hence, even when a user performs a sudden movement, there is no possibility that the force measurement sensor structure 10b excessively reacts sensitively with the movement. Accordingly, it is possible to optimize the support device 29a (operation support device 30c and the muscle strength training support device 30d) within a range suitable for an operation by the user.

Particularly, when the support device 29a is used as the operation support device 30c, by adjusting the first and second elastic members 3a, 3b depending on the content of an operation, it is possible to enhance the above-mentioned characteristics in the upward direction and in the downward direction and hence, a load applied to a user can be reduced.

In the same manner, when the support device 29a is used as the muscle strength training support device 30d, by adjusting the first and second elastic members 3a, 3b depending on a function of a user to be recovered, the above-mentioned loads in the upward direction and in the downward direction can be optimized. That is, the loads optimum for the respective directions can be set. Accordingly, the user can perform training with a load optimum for the upward direction and training with a load optimum for the downward direction simultaneously and hence, a training time can be shortened.

The support device according to this disclosure can, in the case where a force which becomes smaller in a later stage compared to an initial stage, perform support by measuring not the force in an initial stage but the force in the later stage. Here, the support device is applicable to an operation support device and a muscle strength support device which support a human force.

DESCRIPTION OF REFERENCE SIGNS 1 shaft
2 intermediate element
3a first elastic member
3b second elastic member
4 linear potentiometer
5a first end section
5b second end section
6 measurement element
7 fulcrum (rotary shaft)
7a bearing
9 rotational potentiometer
10, 10a, 10b force measurement sensor structure
11 wire
12, 12a gripping unit (grip)
13 hook
14 base
15a, 15b spring receiver
16 motor (drive unit)
18 control unit
20, 20a load control device
21 CPU
22 memory
23 storage unit
24 input unit
25 output unit
26 potentiometer reading unit
27 intermediate element applied force calculation unit
28 elastic member load control unit 29, 29a support device
30a, 30c operation support device
30b, 30d muscle strength training support device
31a, 31b upper arm wearable units
32a, 32b, 36, 38 body wearable unit
33 power source
40 main frame
41 back rest portion
42 shoulder belt
43 waist belt
44 arm
45 front frame
46 rear frame
50 roller
51 hinge portion
52 side bars
53 slide rail
54 slide frame
55 width adjustment unit
56 damper

The invention claimed is:

1. A support device comprising:
a force measurement sensor structure comprising: first and second elastic members; and an intermediate element supported between the first and second elastic members;
a drive unit which is configured to vary a load applied to the intermediate element from the first and second elastic members of the force measurement sensor structure;
a control unit which is configured to control the drive unit; and
a wearable unit which a user wears on the user's body;
wherein the force measurement sensor structure includes:
a shaft having a first end section and a second end section;
the intermediate element movably provided between the first end section and the second end section along the shaft;
the first elastic member provided between the first end section and the intermediate element along the shaft;
the second elastic member provided between the second end section and the intermediate element along the shaft;
a linear potentiometer connected to the intermediate element and configured to detect a position of the intermediate element in one dimensional direction along the shaft; and
a gripping unit connected to the intermediate element and configured to transmit a force to the intermediate element in an interlocking manner with a movement of an upper limb or a lower limb of the user,
the wearable unit includes:
a front frame provided on a front side of the user;
a rear frame connected to the front frame, provided on a rear side of the user, and supporting the drive unit; and
an arm attached on the front frame, the arm suspending a wire which connects the force measurement sensor structure and the drive unit to each other,
wherein the first and second elastic members are configured to support the intermediate element, are capable of applying a load to the intermediate element in directions opposite to each other in one dimensional direction along the shaft,
the linear potentiometer detects a position of the intermediate element in one dimensional direction along the shaft to measure a force applied to the intermediate element, and
the control unit is configured to control the drive unit depending on the measured force applied to the intermediate element.

2. The support device according to claim 1, wherein the drive unit is configured to vary at least one of a magnitude of a load applied to the intermediate element from the first elastic member and the second elastic member and a direction of the load.

3. The support device according to claim 1, wherein the wearable unit includes a rear frame open/close mechanism which is configured to open or close the rear frame.

4. The support device according to claim 3, wherein the rear frame open/close mechanism is constituted of a rotatable hinge portion which connects the front frame and the rear frame, and is configured to open or close the rear frame upward using the hinge portion as a fulcrum.

5. The support device according to claim 4, wherein the rear frame open/close mechanism connects the rear frame and the arm to each other, includes a damper which imparts a buffer action to movement of the rear frame and movement of the arm, and is configured to buffer an open/close operation of the rear frame by the damper in opening or closing the rear frame.

6. The support device according to claim 3, wherein the rear frame open/close mechanism is configured to open or close at least a portion of the rear frame sideward.

7. The support device according to claim 3, wherein the rear frame open/close mechanism is configured to open or close at least a portion of the front frame upward.

8. The support device according to claim 1, further comprising:
a slide rail provided on the front frame; and
a slide frame arranged on the slide rail and relatively movable relative to the front frame by the slide rail.

9. The support device according to claim 1, further comprising a side bar connecting the front frame and the rear frame along a side portion of a user such that a width between the front frame and the rear frame is variable.

10. The support device according to claim 1, wherein the arm is arranged at respective portions of the front frame corresponding to both shoulders of the user, respectively.

11. The support device according to claim 1, further comprising a shoulder belt for supporting the wearable unit by being suspended from a shoulder of the user.

12. The support device according to claim 1, the first and second elastic members are each constituted of one or more kinds of members selected from a group consisting of spring, rubber, and air.

13. An operation support device including: the support device according to claim 1, wherein
the control unit is configured to support a movement of an upper limb or a lower limb of the user by controlling the drive unit such that a measured force applied to the intermediate element is decreased depending on a movement of the upper limb or the lower limb of the user.

14. A muscle strength training support device including: the support device according to claim 1, wherein
the control unit is configured to support muscle strength training of an upper limb or a lower limb of the user by controlling the drive unit such that a predetermined force is applied to the intermediate element depending on a movement of an upper limb or a lower limb of the user.

* * * * *